United States Patent
Yoshida et al.

(10) Patent No.: US 8,410,460 B2
(45) Date of Patent: Apr. 2, 2013

(54) PATTERN DEFECT INSPECTION METHOD AND ITS APPARATUS

(75) Inventors: Minoru Yoshida, Yokohama (JP); Shunji Maeda, Yokohama (JP); Hidetoshi Nishiyama, Fujisawa (JP); Masahiro Watanabe, Yokohama (JP)

(73) Assignee: Hitachi High-Technologies Corporation, Tokyo (JP)

( * ) Notice: Subject to any disclaimer, the term of this patent is extended or adjusted under 35 U.S.C. 154(b) by 461 days.

(21) Appl. No.: 11/785,432

(22) Filed: Apr. 17, 2007

(65) Prior Publication Data

US 2007/0195316 A1  Aug. 23, 2007

Related U.S. Application Data

(63) Continuation of application No. 10/765,920, filed on Jan. 29, 2004, now Pat. No. 7,205,549.

(30) Foreign Application Priority Data

Jan. 29, 2003   (JP) ................................. 2003-020896

(51) Int. Cl.
  *G01J 3/10* (2006.01)
(52) U.S. Cl. .................. 250/504 R; 250/372; 356/237.5
(58) Field of Classification Search ............... 250/504 R
  See application file for complete search history.

(56) References Cited

U.S. PATENT DOCUMENTS

| | | | |
|---|---|---|---|
| 5,479,252 A | 12/1995 | Worster et al. | |
| 5,532,743 A * | 7/1996 | Komobuchi | 348/297 |
| 6,566,671 B1 | 5/2003 | Yoshida et al. | |
| 6,597,448 B1 * | 7/2003 | Nishiyama et al. | 356/237.4 |
| 6,621,571 B1 | 9/2003 | Maeda et al. | |
| 6,800,859 B1 | 10/2004 | Shishido et al. | |
| 7,123,356 B1 * | 10/2006 | Stokowski et al. | 356/237.2 |
| 7,136,159 B2 * | 11/2006 | Tsai et al. | 356/237.5 |
| 2001/0025924 A1 | 10/2001 | Uto et al. | |
| 2002/0067477 A1 * | 6/2002 | Morita et al. | 356/237.5 |
| 2002/0154297 A1 | 10/2002 | Noguchi et al. | |

FOREIGN PATENT DOCUMENTS

| | | |
|---|---|---|
| JP | 61-212708 | 9/1986 |
| JP | 8-320294 | 12/1996 |
| JP | 10-078668 | 3/1998 |
| JP | 10-325805 | 12/1998 |
| JP | 2001-005961 A | 1/2001 |
| JP | 2001-165861 | 6/2001 |
| JP | 2001-176942 | 6/2001 |
| JP | 2001-194323 | 7/2001 |
| JP | 2001-296570 | 10/2001 |
| JP | 2002-039960 | 2/2002 |
| JP | 2002-168799 | 6/2002 |

OTHER PUBLICATIONS

Japanese Office Action dated May 29, 2007.

* cited by examiner

*Primary Examiner* — Phillip A Johnston
(74) *Attorney, Agent, or Firm* — Antonelli, Terry, Stout & Kraus, LLP.

(57) ABSTRACT

The pattern defect inspection apparatus and its method of the present invention comprises: a recipe setting unit for setting an inspection recipe and/or a review recipe; an illumination optical system including: a laser light source for emitting ultraviolet laser light; a quantity-of-light adjusting unit for adjusting a quantity of the ultraviolet laser light emitted from the laser light source; and an illumination range forming unit for forming on a sample an illumination range of the ultraviolet laser light; a coherence reducing system; and a detection optical system including: a condensing optical system; a diffracted-light control optical system; and a detecting unit.

3 Claims, 22 Drawing Sheets

FIG. 12
(a)
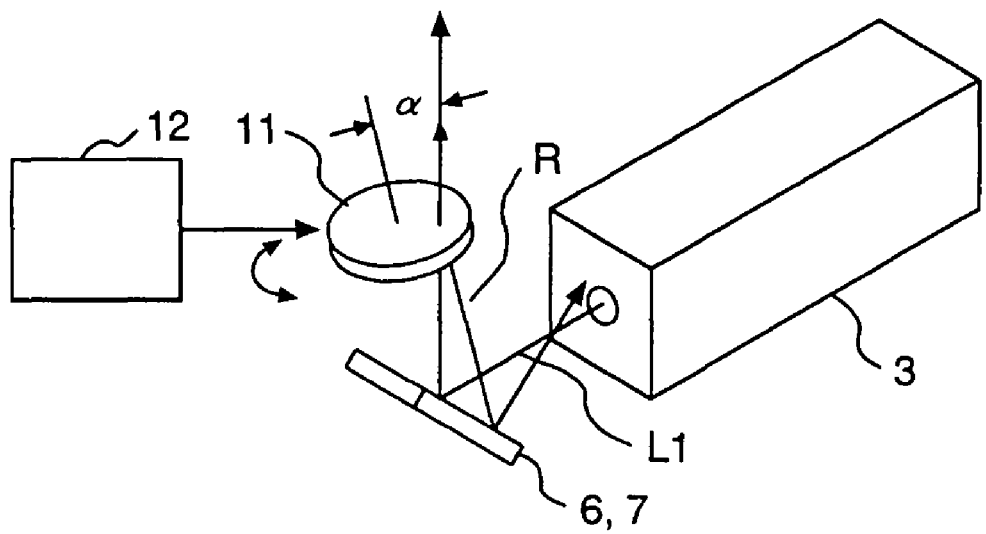
(b)
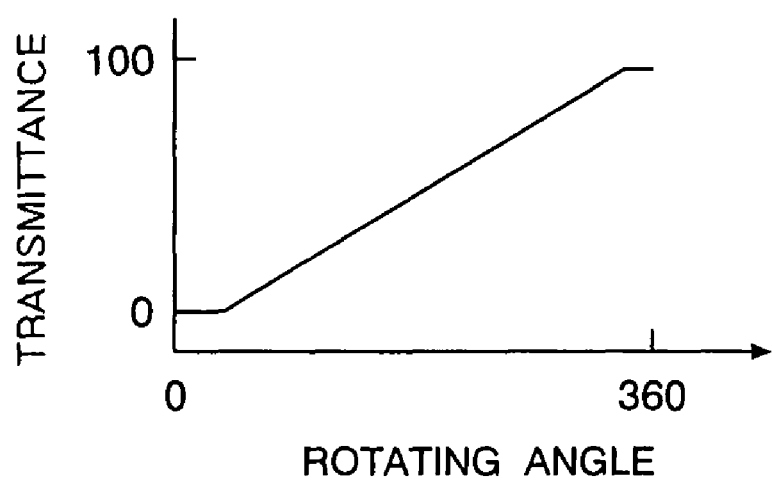

FIG. 17
(a)
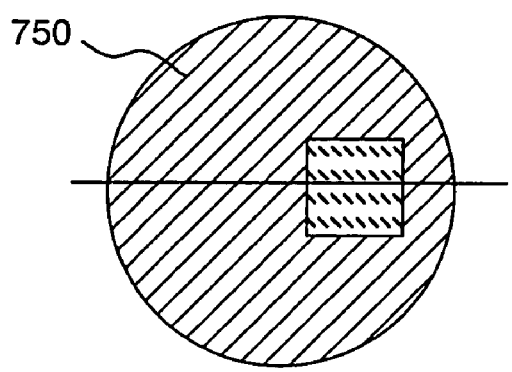
(b)
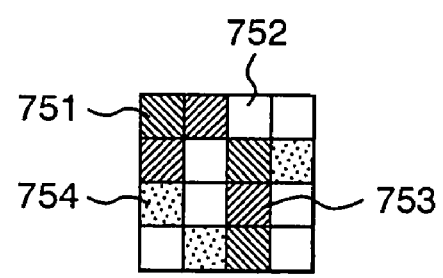
(c)
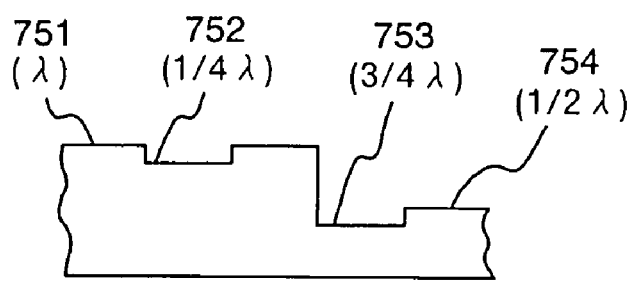
(d)
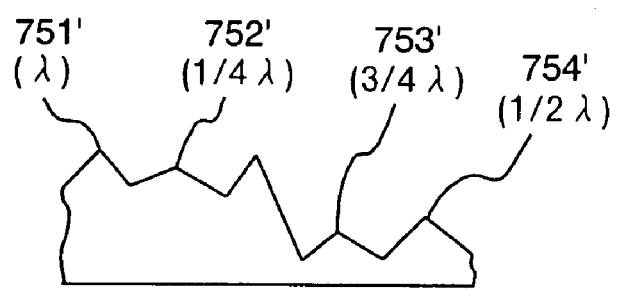

FIG. 26
(a)
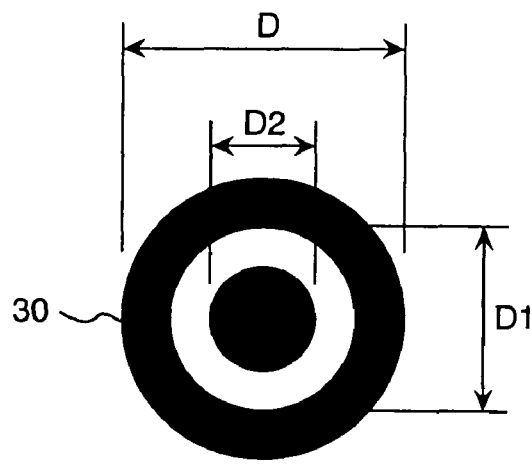
(b) 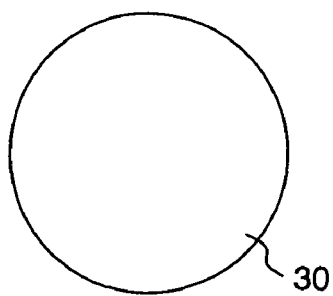
(c) 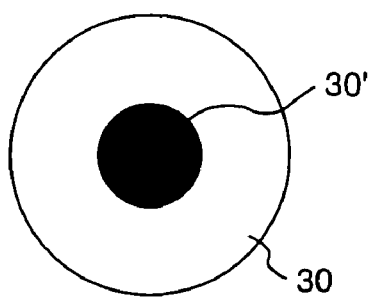
(d) 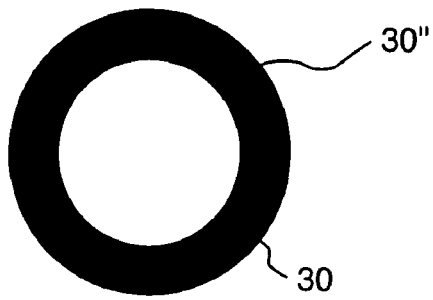

PATTERN DEFECT INSPECTION METHOD AND ITS APPARATUS

CROSS-REFERENCE TO RELATED APPLICATION

This application is a Continuation of U.S. application Ser. No. 10/765,920, filed Jan. 29, 2004 now U.S. Pat. No. 7,205,549, which claims priority from Japanese patent application 2003-020896, filed Jan. 29, 2003, the contents of which are incorporated herein by reference.

BACKGROUND OF THE INVENTION

The present invention relates to pattern inspection and foreign material inspection that detect a defect (including a short circuit and a broken wire) and a foreign material of a pattern to be inspected. More particularly, it relates to an inspected-pattern defect inspection method, and its apparatus, used for inspecting a defect and a foreign material on a pattern to be inspected such as a semiconductor wafer, a liquid crystal display, and a photo mask. The description below is based on the assumption that a defect includes a foreign material.

Japanese Patent Laid-open No. 8-320294 (prior art 1) is known as the prior art relating to defect inspection of a pattern to be inspected. This prior art 1 describes the technology comprising the steps of: in a pattern to be inspected such as a semiconductor wafer where an area with high pattern density such as a memory mat unit and an area with low pattern density such as a peripheral circuit are mixed in a chip, on the basis of the frequency distribution of brightness on the detected image, analog-to-digital converting the detected image signal to obtain a digital image signal, and then gray-scale converting the digital image signal so that brightness or contrast between the high density area and the low density area of the pattern to be inspected becomes a value of the predetermined relationship; making a comparison in a state in which this gray-scale converted image signal is aligned with an gray-scale converted image signal to be compared; and thereby inspecting a minute defect with a high degree of accuracy.

In addition, the technology described in Japanese Patent Laid-open No. 10-78668 (prior art 2) is known as the prior art relating to inspection of a pattern on a photo mask. According to this prior art 2, a UV laser such as an excimer laser is used as a light source. In the description, a mask is evenly irradiated with the UV light, coherence of which is reduced by rotating a diffusing plate inserted into an optical path, and then a feature index is calculated from obtained image data of the mask to judge whether or not the photo mask contains a defect.

Moreover, Japanese Patent Laid-open Nos. 2001-176942, 2001-194323☐U.S. Pat. No. 6,621,571☐, and 2001-296570 (U.S. application Ser. No. 09/764,457) are further known as the prior art relating to a pattern defect inspection apparatus using UV or DUV laser light. In recent years, in the field of the LSI production, circuit patterns formed on a wafer are microminiaturized as high integration demands. Its pattern width, therefore, is reduced to 200 nm or less, which reaches the resolution limit of an image-formation optical system. Accordingly, an increase in NA of the image-formation optical system is being made, and an optical superresolution technology is being applied.

However, the increase in NA reaches the physical limit. Because of it, making a wavelength used for detection shorter, more specifically, using wavelength bands of ultraviolet light (UV light) and far-ultraviolet light (DUV light), is an essential approach.

On the contrary, as a wavelength of a light source of an exposure apparatus for copying a pattern is made shorter, the shorter wavelength also involves the sensitivity of resist. Accordingly, the sensitivity to an exposure wavelength is the highest. Thus, when an inspection wavelength extremely gets close to the exposure wavelength, the resist reacts at the time of inspection, causing a pattern to shrink or expand. Accordingly, there is a possibility that the pattern will be damaged. It is known that in a typical review using a secondary electron such as SEM, the density of energy applied to a wafer is high, and therefore, a size called shrinkage varies.

Also judging from this, although the energy density is low as compared with the SEM, a wavelength of light to be irradiated is close to, or the same as, an exposure wavelength of the resist. Therefore, it is probable that there is some influence.

Moreover, in a memory part having a narrow line width like a system LSI, or in a chip where a rough wiring part is mixed, irradiating with inspection light causes heat to accumulate in part of the chip. Therefore, there is also concern that the bimetal effect will cause peeling of a pattern called stress migration.

Further, in recent years, if a design rule becomes 100 nm or less, it is necessary to use a material with low conductivity (low-k). In the case of the material with low conductivity, its film becomes softer. This means a decrease in mechanical strength, resulting in low adhesion at the time of deposition. Accordingly, the peeling of a pattern is liable to occur as described above. As the material with low conductivity, many kinds of materials including $Cu/SiO_2$ and Cu/SiOF are used for wiring of Cu. Usually, SiOC and SiON are used to form a barrier layer. Further microminiaturization makes it possible to produce a thinner material with ultra low conductivity, having low ratio conductivity. Because new materials are being developed, thinner materials are used in future. At all events, soft film is a common property. Not only the peeling but also diffusion by heat, chemical change by ultraviolet light of impurities, and the like, may influence the film. Therefore, there is a possibility that a bad influence will be exerted on a device.

In addition, there is a limit of the heat capacity that is acceptable for the device, which is called thermal budget. Taking stress by heat into consideration, this is a period of time during which a device structure does not change. This includes, for example, anneal time, and a step of thermal diffusion. It is also probable that when heat is applied by inspection, the limiting value is exceeded, exerting an influence on a manufacturing process of the device.

Further, also at the time of inspection, it is necessary to perform inspection at high speed. Therefore, it is not possible to use a method in which a thinly narrowed laser beam is scanned on a sample. On the other hand, if illumination with a laser beam is performed with a visual field being fully opened, a speckle occurs. In addition to it, overshoot and undershoot called ringing also occur in the edge part of a circuit pattern. Therefore, a high-quality image cannot be obtained.

SUMMARY OF THE INVENTION

The present invention has been made to solve the problems, and an object of the present invention is to provide a pattern defect inspection method, and its apparatus, used to detect a minute circuit pattern with high resolution at high speed by use of ultraviolet light or ultraviolet laser light without causing the damage to a device as a target to be inspected, and thereby to detect a defect.

Another object of the present invention is to provide a manufacturing method of a semiconductor device, by which a super minute semiconductor device can be manufactured using the pattern defect inspection method and its apparatus.

According to one aspect of the present invention, there is provided a pattern defect inspection apparatus (including a pattern defect review apparatus). The pattern defect inspection apparatus comprises: a recipe setting unit for setting an inspection recipe and/or a review recipe; an illumination optical system including: a laser light source for emitting ultraviolet laser light; a quantity-of-light adjusting unit for adjusting the quantity of the ultraviolet laser light emitted from the laser light source in accordance with the inspection recipe and/or the review recipe set by the recipe setting unit; an illumination range forming unit for forming in a sample an illumination range of the ultraviolet laser light whose quantity has been adjusted by the quantity-of-light adjusting unit; a coherence reduction optical system for reducing coherence of the ultraviolet laser light received within the illumination range that has been formed by the illumination range forming unit; and an irradiation optical system for irradiating the sample with the ultraviolet light flux whose coherence has been reduced by the coherence reducing system; and a detection optical system including: a condensing optical system for condensing reflected light from the sample; a diffracted-light control optical system for controlling diffracted light of the reflected light that has been condensed by the condensing optical system; and a detector for imaging a reflected light image coming from the sample to detect an image signal, the reflected light image being obtained through the diffracted-light control optical system.

In addition, according to the present invention, an ultraviolet light source or an ultraviolet laser light source is used as a light source. There is provided a means for preventing a speckle of ultraviolet light or a speckle of ultraviolet laser light from occurring in an optical path. It is so devised that an image of an object is detected by irradiating a surface of the object with the ultraviolet light for which the coherence by the speckle is reduced. Here, it is assumed that the ultraviolet light includes far-ultraviolet light. According to the present invention, as the unit for preventing a speckle of the ultraviolet light from occurring, a diffusing plate is placed, and a means (an unit) for making a movement that is relative to luminous flux is provided in a direction substantially perpendicular to an optical axis. Moreover, for the purpose of improving the pattern contrast, paying attention to the fact that a polarized state of laser light can be freely controlled, it becomes possible to detect part of a polarized component of detected light by controlling a direction and ellipticity of polarization of illumination light.

That is to say, according to the present invention, in order to achieve the above-mentioned purposes, there is provided a pattern defect inspection apparatus. This apparatus comprises a light source for emitting ultraviolet light, laser light, or ultraviolet laser light; an optical path interception unit for intercepting the ultraviolet light, the laser light, or the ultraviolet laser light, which has been emitted from the light source; a measuring unit for measuring an optical axis of the ultraviolet light, of the laser light, or of the ultraviolet laser light, which has been emitted from the light source; a quantity-of-light adjusting unit for adjusting the quantity of the ultraviolet light, of the laser light, or of the ultraviolet laser light, which has been emitted from the light source; an illumination range forming unit for forming an illumination range of the ultraviolet light, of the laser light, or of the ultraviolet laser light, which has been emitted from the quantity-of-light adjusting unit; an irradiation system for reducing coherence of the ultraviolet light, of the laser light, or of the ultraviolet laser light, which has been emitted from the illumination range forming unit, before illuminating a sample with the light whose coherence has been reduced; an image detecting system for imaging the sample to detect an image signal, the sample being irradiated with the laser light by the irradiation system; and a defect detecting unit for detecting a defect of a pattern formed on the sample on the basis of information about the image signal of the sample which has been detected by the image detecting system.

According to another aspect of the present invention, there is provided a pattern defect inspection method comprising an illumination step; and a detection step. The illumination step further includes the sub-steps of: adjusting the quantity of ultraviolet laser light emitted from a laser light source by a quantity-of-light adjusting unit in accordance with a state of a sample; forming by an illumination range forming unit an illumination range of the adjusted ultraviolet laser light in the sample; reducing by a coherence reduction optical system coherence of the ultraviolet laser light received within the formed illumination range; and irradiating by an irradiation optical system the sample with the ultraviolet light flux whose coherence has been reduced. The detection step further includes the sub-steps of: condensing reflected light coming from the sample by a condensing optical system; controlling diffracted light of the condensed reflected light by a diffracted-light control optical system; and imaging by a detector a reflected light image from the sample to detect an image signal, the reflected light image being obtained by the control.

According to still another aspect of the present invention, there is provided a pattern defect inspection method. The pattern defect inspection method comprises the steps of: irradiating a wafer having a diameter of 300 mm with ultraviolet laser light whose coherence has been reduced; imaging the wafer, which has been irradiated with the ultraviolet laser light, to detect an image of the wafer; and handling the detected image of the wafer, which has been irradiated with the ultraviolet laser light, to detect a defect having a size of about 100 nm or less in a pattern formed on the wafer with a throughput of three pieces of wafers or more per hour.

These and other objects, features and advantages of the invention will be apparent from the following more particular description of preferred embodiments of the invention, as illustrated in the accompanying drawings.

BRIEF DESCRIPTION OF THE DRAWINGS

FIG. 12 is explanatory diagrams illustrating one embodiment of an ND filter mechanism according to the present invention;

FIG. 17 is explanatory diagrams illustrating a random phase plate according to the present invention;

FIG. 26 is diagrams illustrating a detection diaphragm (detection filter) according to the present invention;

DESCRIPTION OF THE PREFERRED EMBODIMENTS

Figure 1:
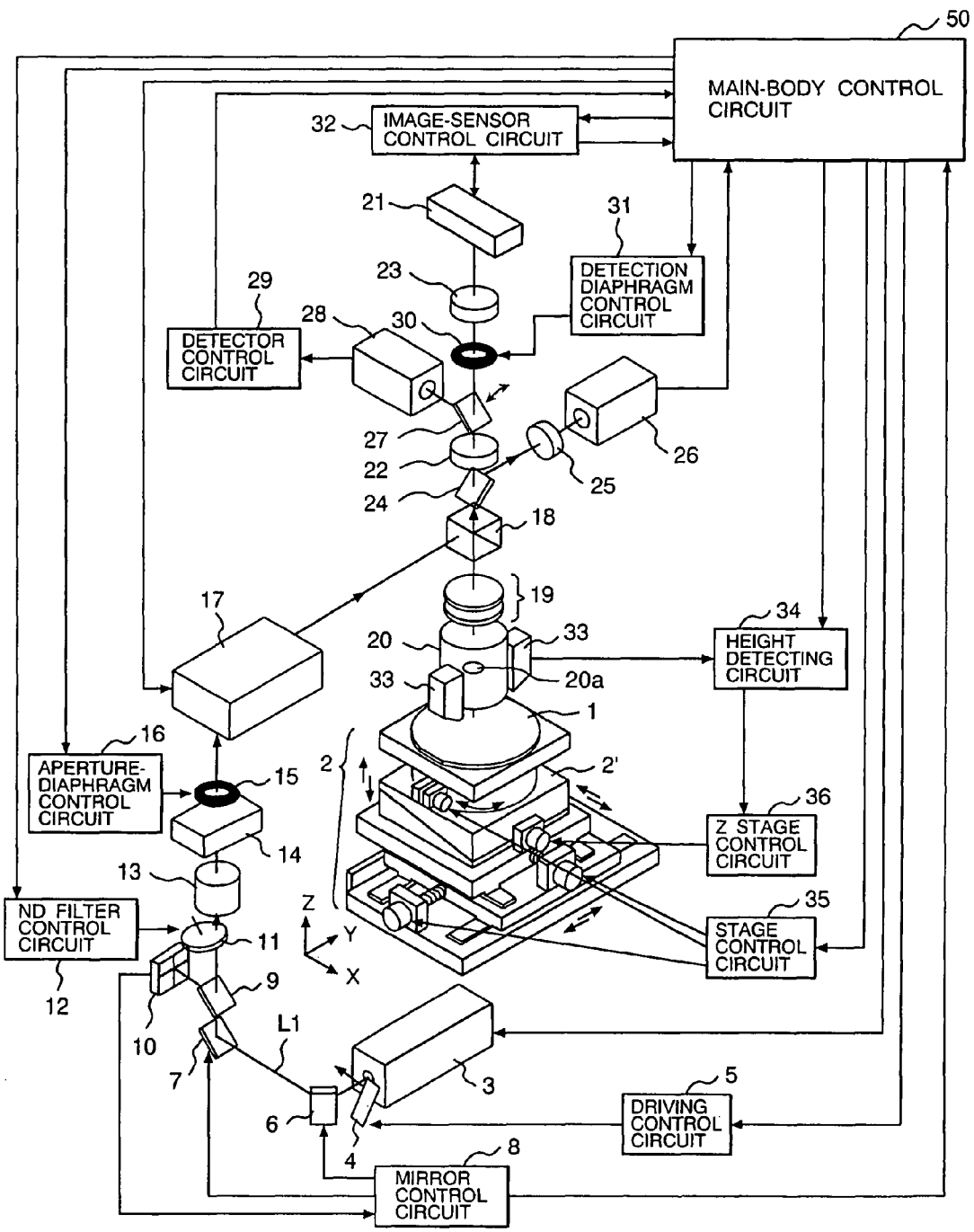
FIG. 1 is a configuration diagram illustrating one embodiment of a defect inspection apparatus for inspecting a pattern to be inspected according to the present invention.

Embodiments of a defect inspection method for inspecting a pattern to be inspected, and of its apparatus, according to the present invention, will be described with reference to drawings. FIG. 1 is a diagram illustrating one embodiment of the apparatus according to the present invention. A stage 2 is constituted of X, Y, Z, and θ (rotation) stages. A semiconductor wafer (sample) 1 which is an example of a pattern to be inspected is placed on the stage 2.

An illumination optical system is formed of an irradiation optical system comprising: an illumination light source 3; a shutter 4 that is one of quantity-of-light adjusting unit, and that can switch the quantity of light between a state close to ON and a state close to OFF; mirrors 6, 7 for adjusting optical axis displacement; an ND filter 11 that is one of quantity-of-light adjusting unit; a beam expander 13; an illumination-range formation optical unit 14 for forming a multipoint secondary light source; an aperture diaphragm 15 for adjusting NA (σ); a coherence reduction optical system 17; a split prism 18; and an objective lens 20.

Since a pattern to which a design rule of about 70 nm or less is applied is formed on the sample 1, for example, an ultraviolet or far-ultraviolet laser light source whose wavelength is 266 nm or 355 nm is adopted as the illumination light source 3. The ultraviolet laser light source is composed of a device that converts a wavelength of a solid YAG laser beam by a nonlinear optical crystal or the like to generate the third harmonic (355 nm) or fourth harmonic (266 nm) of a fundamental harmonic. In addition, a laser light source having a wavelength of 193 nm, 195 nm, or 248 nm may also be used. Moreover, a wavelength of 100 nm or less may also be used if such a wavelength exists as a wavelength of a laser light source. The wavelength of 100 nm or less leads to an improvement in resolution. Incidentally, although either the continuous oscillation or the pulse oscillation can be adopted as a laser oscillation mode, the continuous oscillation is desirable. It is because the stage is continuously moved to detect an image from the target 1. The stage 2 can be controlled in X, Y, and θ directions by a stage control circuit 35 using an unillustrated method. A Z stage 2' can be controlled in a Z direction by a Z stage control circuit 36 using an unillustrated method.

The shutter 4 can switch an optical path of luminous flux L1 coming from the illumination light source 3 between a state close to passing (ON) or a state close to interception (OFF). The driving control circuit 5 can control the movement of the shutter 4 in an arbitrary period of time. Incidentally, the shutter 4 is not required to completely intercept the luminous flux L1. Achieving a state in which the luminous flux L1 is almost entirely intercepted (in other words, the quantity of light is remarkably decreased) suffices. To be more specific, a shutter capable of remarkably changing the quantity of light on a time basis can be adopted as the shutter 4. In addition, a shutter comprising an acoustooptic modulator (AOM) such as an optical deflector, in which the acoustooptic modulator is driven by the driving control circuit 5 to change deflection of light so that the quantity of light can be immediately and remarkably changed, can also be adopted as the shutter 4.

An optical axis of the luminous flux L1 passing through the shutter 4 can be adjusted up and down, and right and left, by use of the mirrors 6 and 7. The mirrors 6 and 7 can be moved up and down, and right and left, using an unillustrated method. An optical-path splitting mirror 9 is placed in such a manner that part of the quantity of light of the luminous flux L1 can be taken out, and that its reflected light is projected onto a split sensor 10. The split sensor 10 detects a position of the optical axis of the luminous flux L1. When the split sensor 10 detects that the position is displaced from a given position, a mirror control circuit 8 can control the movement of the mirrors 6, 7.

Figure 27:
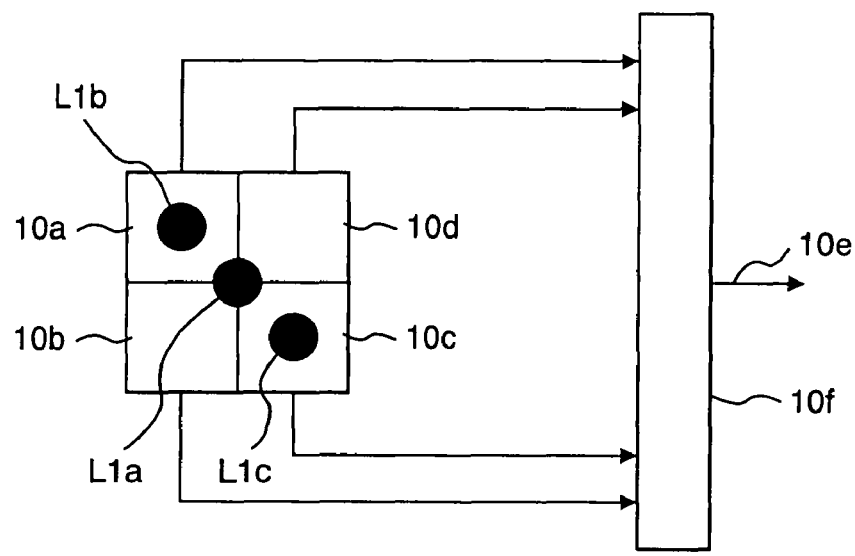
FIG. 27 is a diagram illustrating a split sensor for reviewing an optical axis according to the present invention.

FIG. 27 is a diagram illustrating an embodiment of the split sensor 10. The split sensor 10 is, for example, a four-way split sensor. The outputs of sensors 10a, 10b, 10c, 10d are sent to an amplifier circuit 10d, and then a signal 10e is sent to the mirror control circuit 8 using an unillustrated method. For example, when the luminous flux L1 is at the center, the center of the split sensor 10, which corresponds to a position L1a, is irradiated with the luminous flux L1. At this time, the outputs of the sensors become the same. Accordingly, the signal 10e is not sent to the mirror control circuit 8. When the luminous flux L1 moves due to fluctuations, which causes an irradiated position to shift to a position L1b or a position L1c, the outputs of the sensors change. As a result, the signal 10e is sent to the mirror control circuit 8. In this case, a direction of the change, and the quantity of the change, can be judged from the irradiated position. Therefore, it is possible to prevent optical axis displacement of the luminous flux L1 emitted from the illumination light source 3 by controlling and moving the mirrors 6, 7 using an unillustrated method so that the luminous flux L1 always comes to the position L1a.

Next, the ND filter 11 for limiting the quantity of light controls the quantity of light of the luminous flux L1 so that it is limited to the quantity of light required for inspection. The ND filter 11 can be driven and controlled according to an instruction of an ND filter control circuit 12 using an unillustrated method. This ND filter 11 can also have a function of the shutter 4 if this ND filter 11 is provided with a filter that is almost light proof. In short, although there is a difference in switching speed among the shutter 4, the ND filter 11, and the optical deflector, they are all the same from a viewpoint that the quantity of light can be adjusted on a time basis (quantity-of-light adjusting unit). Incidentally, in this embodiment, the quantity of light during the inspection is adjusted by the ND filter 11, whereas the quantity of light during the review is adjusted by the shutter 4 including an optical deflector (a state in which light is almost intercepted is achieved).

Next, the beam expander 13 expands the luminous flux L1 so that its size becomes equivalent to the size of a pupil 20a of the objective lens 20. Next, the illumination-range formation optical unit 14 forms (determines) an illumination range of the expanded luminous flux on the sample 1. Next, the aperture diaphragm 15 limits NA incident on the pupil 20a of the objective lens 20. To be more specific, the aperture diaphragm 15 is placed at a position conjugated with the pupil 20a of the objective lens 20 so as to limit NA incident on the pupil 20a. The aperture diaphragm 15 can be driven and controlled according to an instruction of an aperture-diaphragm control circuit 16 using an unillustrated method.

Next, the luminous flux passes through the coherence reduction optical system 17. The luminous flux is then led to the objective lens 20 by the split prism 18. The coherence reduction optical system 17 is used to reduce the coherence of a laser beam emitted from the illumination light source 3. Here, an optical system capable of reducing time coherence or spatial coherence can be adopted as the coherence reduction optical system 17. The coherence reduction optical system 17 can be configured as, for example, a mechanism for scanning on the pupil 20a of the objective lens 20 a laser beam coming from the illumination light source 3.

The split prism 18 is formed of a polarization beam splitter as the case may be. The split prism 18 is devised to reflect illumination light coming from the illumination light source 3, and thereby to provide the sample 1 with, for example, bright field illumination through the objective lens 20. In this manner, the optical system from the split prism 18 up to the objective lens 20 is designated as an irradiation optical system. If the split prism 18 is formed of the polarization beam splitter, the split prism 18 has the following working: when the polarization direction of illumination light is parallel to a reflection plane, it reflects; and when the polarization direction of illumination light is perpendicular to the reflection plane, it passes through the reflection plane. Accordingly, if a laser beam is used as the illumination light source 3, it becomes possible to totally reflect the laser beam by the split prism 18 because the laser beam is a polarization laser beam from the beginning.

A polarization element group 19 which is a unit for controlling a diffraction image from the sample is placed at a position conjugated with, or in proximity to, the sample. The polarization element group 19 has a function of controlling the polarization directions of the illumination light and the reflected light to arbitrarily adjust a polarization ratio of the illumination light using an unillustrated method so as to prevent the reflected light from reaching an image sensor 21 as a result of irregularity in brightness caused by a difference in pattern shape and a difference in pattern density. The polarization element group 19 includes, for example, a half-wave plate and a quarter-wave plate. By controlling rotation of each of the half-wave plate and the quarter-wave plate about an optical axis to set a rotation angle, a polarized state of the reflected light emitted from a circuit pattern formed on the sample 1 is controlled; in other word, diffracted light of the reflected light is controlled. For example, the image sensor 21 can detect such diffracted light that zero-order diffracted light is attenuated whereas high-order diffracted light is little attenuated. As a result, pattern contrast is dramatically improved, making it possible to achieve stable sensitivity. That is, the polarizer group 19 serves as a diffracted-light control unit for controlling diffracted light of reflected light.

The sample 1 is irradiated with illumination light coming through the objective lens 20 that constitutes the irradiation optical system. Its reflected light is entered into the objective lens (condensing optical system) 20 again. It is so devised that an image of the reflected light is formed on the image sensor 21 by use of an image formation lens 22 and a relay lens 23. That is, an image-formation optical system comprises the image formation lens 22 and the relay lens 23. The image sensor 21 has a pixel size of about 0.05 to 0.3 µm when making a conversion on the sample. The image sensor 21 outputs a gray-scale image signal in accordance with brightness (gray scale) of the reflected light coming from the sample 1 that is an example of a pattern to be inspected. It is to be noted that although a refraction type lens may be used as the objective lens 20, a reflection type objective lens may also be used.

Figure 28:
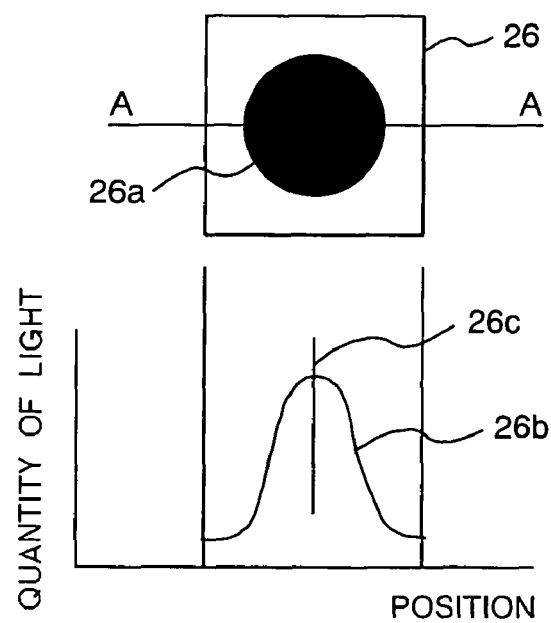
FIG. 28 is diagrams illustrating a review example in which a pupil according to the present invention is reviewed.

Moreover, a beam splitter 24 is disposed in an optical path between the split prism 18 and the image formation lens 22 so that the reflected light passes through a lens 25. As a result, it becomes possible to review the pupil 20*a* of the objective lens 20 by use of a detector 26, e.g., a CCD camera. For example, by reviewing the pupil 20*a* of the objective lens 20 by use of the detector 26, it is possible to prevent the optical axis displacement of the light source as described above. FIG. 28 is a diagram illustrating an embodiment of the review of the pupil 20*a* by use of the detector 26.

A detected image 26*a* of the pupil 20*a* is imaged on the detector 26. A waveform 26*b* is detected along a cross section A-A. For example, by determining the center-of-gravity position 26*c* of this waveform 26*b* with the optical axis aligned therewith, the beam splitter 24 can reduce the reflection level to about 5% for example. Thus, by providing optical properties by which almost all light passes through, no influence is exerted on the quantity of light for inspection.

Additionally, a mirror (switching optical system) 27 is inserted into an optical path between the image formation lens 22 and the relay lens 23. The luminous flux reflected by the mirror 27 is introduced into, for example, a detector 28 such as a CCD camera provided at an image formation position of the image formation lens 22. That is, it becomes possible to review an image of the sample 1 by use of the detector 28. The detector 28 can control imaging timing by use of the detector control circuit 29. It is to be noted that this mirror 27 can be inserted into or ejected from the optical path by use of an insertion/ejection mechanism (not illustrated). This mirror 27 is being ejected during inspection so that no influence is exerted on the quantity of light for inspection. Thus, because the relay lens 23 is disposed between the image formation lens 22 and the image sensor 21, with the image-formation magnification being switched between the detector 28 and the image sensor 21, imaging becomes possible. When the detector 28 performs imaging, the mirror 27 is inserted into the optical path. On the other hand, when the image sensor 21 performs imaging, the mirror 27 is ejected from the optical path, which enables the switched use. In particular, if it is required to get an enlarged image during review, it is needed only to increase the magnification of an image to be detected by the detector 28.

In addition, a detection diaphragm 30 is placed at a position conjugated with the pupil 20*a* of the objective lens 20. Under the control of a detection-diaphragm control circuit 31 and by use of an unillustrated method, the detection diaphragm 30 can control a diameter of the pupil 20*a* at the time of detection. Under the control of an image-sensor control circuit 32, the image sensor 21 can control instructions such as driving speed and timing.

Moreover, in order to continuously aligning a focus position of the objective lens 20 with the surface of the sample 1, an automatic focus detection system 33 is provided in an area adjacent to the objective lens 20. The automatic focus detection system 33 detects the height of the sample 1, and the height is then measured by a height detecting circuit 34. After that, inputting a deviation of the height to a Z stage control circuit 36 permits the Z stage 2' to be controlled, and thus the height of the sample 1 can be aligned.

A main-body control circuit 50 controls all of the control circuits described above, and handles a signal from the image sensor 21.

Incidentally, these optical systems are developed on an optical stand (not illustrated), and are configured in a manner that the optical systems including the light source, the illumination optical system, the detection optical system, and the image sensor are integrated into one unit. For example, the optical stand has a shape of a gate, and with the placement that does not interfere a moving range of the stage 2, the optical stand is disposed on a surface plate mounted with the stage 2 thereon. Accordingly, stable detection can be achieved against disturbance caused by a change in temperature, oscillations, and so on.

With the above-mentioned configuration, ultraviolet light (for example, ultraviolet laser light) L1 emitted from the illumination light source 3 is reflected by the mirror 6, 7, and then passes through the ND filter 11 for limiting the quantity of light. Next, the ultraviolet light is expanded by the beam expander 13, and passes through the coherence reduction optical system 17, the split prism 18, and the polarization element group 19 before entering the objective lens 20. Consequently, the sample (semiconductor wafer) 1 is irradiated with the ultraviolet light. To be more specific, after the ultraviolet light is condensed onto the pupil 20*a* of the objective lens 20, Koehler illumination of the ultraviolet light is performed on the sample 1. Reflected light from the sample 1 passes through the objective lens 20, the polarization element group 19, the split prism 18, the image formation lens 22, and the relay lens 23, and is then detected by the image sensor 21 from vertically above the sample 1.

At the time of inspection, while scanning the stage 2 to move the sample 1 at a constant speed, a focus detection system 33 continuously detects a Z-direction position of an inspection surface of the sample 1, and thereby controls the Z stage 2' in the Z direction so that an interval between the inspection surface and the objective lens 20 becomes constant. The image sensor 21 detects brightness information (gray-scale image signal) of the pattern to be inspected formed on the sample 1 with a high degree of accuracy.

As described above, it becomes possible to inspect a defect of a pattern formed on the sample by the following steps: emitting ultraviolet laser light whose coherence is reduced to the surface of the sample; obtaining an image signal by imaging the surface of the sample to which the ultraviolet laser light is emitted; handling the image signal to detect a defect having a size of 100 nm or less on the sample; and outputting information about a position of the detected defect having a size of 100 nm or less on the sample.

Figure 2:
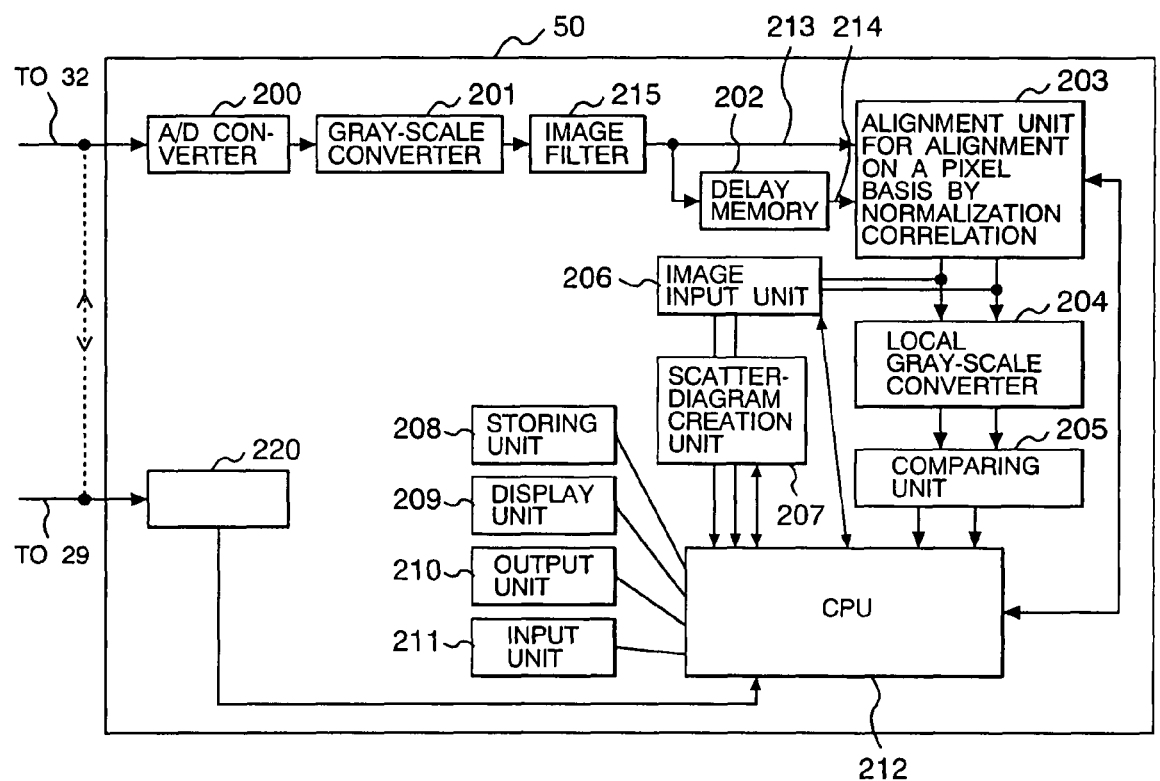
FIG. 2 is a configuration diagram illustrating one embodiment of a main-body control circuit including an image processing unit of the defect inspection apparatus for inspecting a pattern to be inspected according to the present invention.

FIG. 2 is a diagram illustrating one embodiment of the main-body control circuit 50 of the apparatus according to the present invention. The main-body control circuit 50 comprises an A/D converter 200, a gray-scale converter 201, an image filter 215, a delay memory 202, an alignment unit 203, a local gray-scale converter 204, a comparing unit 205, a CPU 212, an image input unit 206, a scatter-diagram creation unit 207, a storing unit 208, a display unit 209, an output unit 210, and an input unit 211. Here, the A/D converter 200, the gray-scale converter 201, the image filter 215, the delay memory 202, the alignment unit 203, the local gray-scale converter 204, and the comparing unit 205 constitute an image processing unit.

The A/D converter 200 converts a gray-scale image signal 21' obtained from the image sensor 21 into a digital image signal, and then outputs it as an image signal of the sample. For example, a 10-bit A/D converter is used as the A/D converter 200.

The gray-scale converter 201 performs the gray-scale conversion as described in Japanese Patent Laid-open No. 8-320294 on the 10-bit digital image signal output from the A/D converter. That is, the gray-scale converter 201 performs the logarithmic transformation, the index transformation, the polynomial transformation, and the like, so as to correct the image. For example, the gray-scale converter 201 is devised to output the corrected image by an 8-bit digital signal. The image filter 215 is a filter that efficiently eliminates distinctive noise of the image detected with the ultraviolet light from the image that has been gray-scale converted for correction.

The delay memory 202 is a storage unit for storing a digital reference image signal. The delay memory 202 stores a digital image signal coming from the image filter 215 to delay the image signal. Each unit of storing corresponds to one cell, a plurality of cells, one chip, or a plurality of chips, each repeating and constituting a semiconductor wafer. Here, the cell is a unit of a pattern repeated in a chip. It is to be noted that the image filter 215 may also be disposed at a position downstream of the delay memory 202.

The alignment unit 203 is a unit used to detect by normalization correlation the quantity of displacement between the digital image signal 213 (digital detection image signal obtained from the sample) output from the gray-scale converter 201, on which the gray-scale conversion has been performed, and the digital delay image signal 214 (digital reference image signal used as a reference) obtained from the delay memory 202, and thereby to make an alignment on a pixel basis.

The local gray-scale converter 204 is a unit used to gray-scale convert both of, or one of, image signals between which feature indices (brightness, a differential value, a standard deviation, texture, etc.) differ from each other so that the difference in the feature indices is eliminated between the image signals.

The comparing unit 205 is a unit used to compare the digital image signal (detection image signal), which has been gray-scale converted in the local gray-scale converter 204, with the reference image signal, and thereby to detect a defect on the basis of the difference in the feature indices. More specifically, the comparing unit 205 compares the detection image signal detected with the reference image signal that has been delayed only by the quantity equivalent to a cell pitch which is output from the delay memory 202. To be more specific, the image processing unit outputs information about the result of the comparison (a difference image, or feature indices determined by judging the difference image on the basis of threshold values) to the CPU 212.

If coordinates such as array data on the sample 1 are inputted through the input unit 211 including a keyboard and a disk, the CPU 212 can create defect inspection data (a position of a defect, and information about its dimensions) on the basis of the coordinates such as the array data on the sample 1, and can store the defect inspection data in the storing unit 208. This defect inspection data can also be displayed on the display unit 209 such as a display as the need arises, and can also be output to the output unit 210. In addition, various kinds of driving units including the stage 2 can be controlled in accordance with inspection conditions and an inspection state. Incidentally, the configuration detailed in Japanese Patent Application Laid-open No. 61-212708, or the like, may be applied to the comparing unit 205. For example, the comparing unit 205 comprises the following circuits: an image alignment circuit for aligning an image; a difference-image detecting circuit for detecting a difference image of the aligned image; a mismatch detecting circuit for binarizing the difference image; and a feature extraction circuit for calculating an area, a length (projected length), coordinates, and the like, from the binarized output.

The image input unit 206 is a unit for inputting images in synchronization or in asynchronization so as to create a scatter diagram of both images that have been aligned on a pixel basis by the alignment unit 203. The scatter-diagram creation unit 207 creates a scatter diagram for both of the images inputted by the image input unit 206 on the basis of feature indices of a categorized detected image and feature indices of a reference image, and then displays the scatter diagram on, for example, the display unit 209. Incidentally, the image processing unit may also be configured as a plurality of units having a plurality of respective algorithms, in which the algorithm, or a threshold value for judgment, can be selected automatically or according to an instruction.

Figure 3:
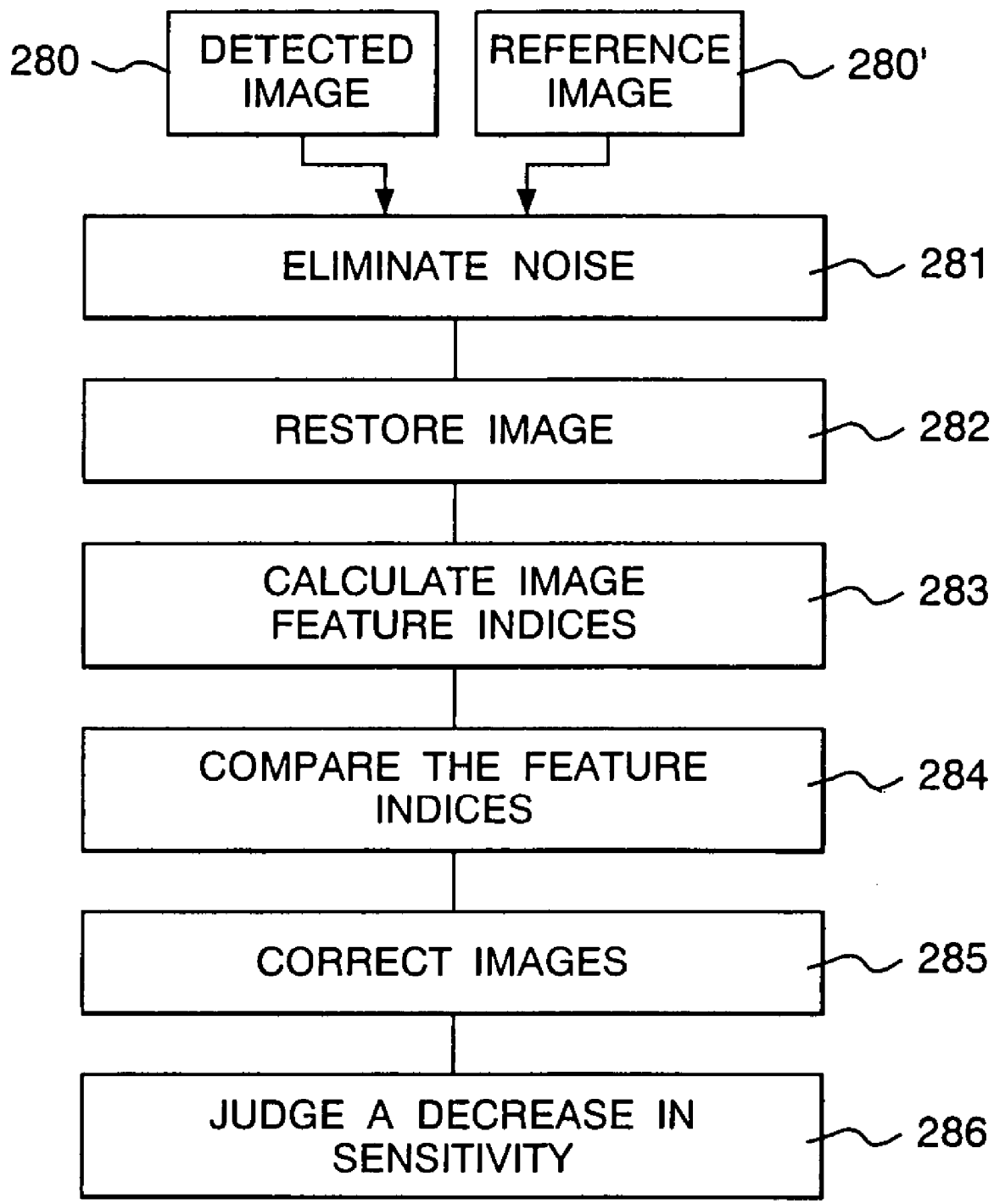
FIG. 3 is an explanatory diagram illustrating processing of an image filter of the image processing unit according to the present invention.

FIG. 3 is a flowchart illustrating an example of image processing by the apparatus according to the present invention. Here, an example of the image filter 215 will be described. To begin with, as the need arises, noise of inputted images 280, 280' are eliminated and the image quality of the images is improved so that an S/N ratio is improved. Various kinds of filters are prepared for the noise elimination (step 281), and they are selectable in accordance with an object or the quality of noise. Its example is a method in which proximate values are used by assigning weights to the respective values. In actuality, for a target pixel, each of proximate values (n×m) is multiplied by a filter coefficient, which is then added.

Figure 4:
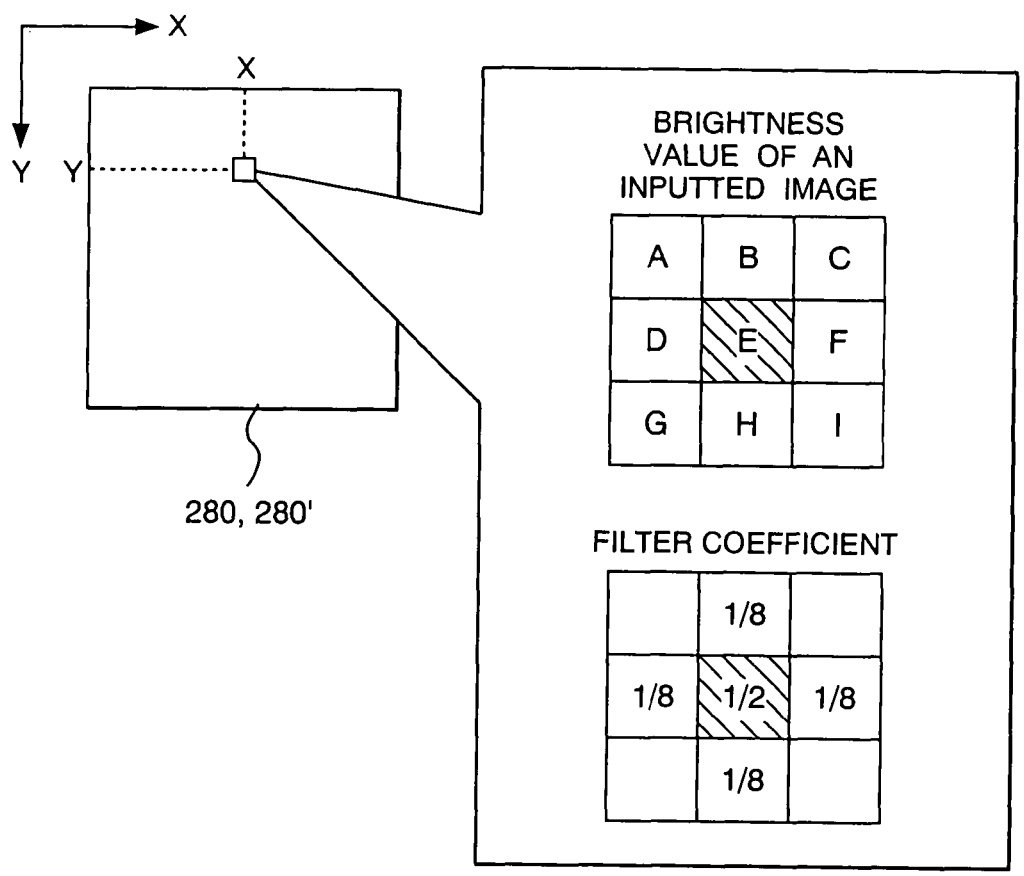
FIG. 4 is an explanatory diagram illustrating the image filter of the image processing unit according to the present invention.

FIG. 4 is a flowchart illustrating an example of filtering of image processing by the apparatus according to the present invention. FIG. 4 shows a case in which assuming that m=n=3, a weight of each proximate pixel value is ⅛. A value of the target pixel can be calculated by Equation 1.

$$F(i,j)=B\square\tfrac{1}{8}+D\square\tfrac{1}{8}+F\square\tfrac{1}{8}+H\square\tfrac{1}{8}+E\square\tfrac{1}{2} \qquad \text{(Equation 1)}$$

The size and coefficient of the filter can be flexibly changed by use of a lookup table. Another example is a median filter. The median filter uses a median of brightness values within a predetermined proximity, which makes it possible to exclude the influence of irregular values. In addition, there is also an example that uses the Gaussian function. Here, to begin with, the two-dimensional Gaussian function (Equation 2) in which an average=0 and distribution=$\sigma^2$ is performed convolution operation for an image f(x, y) by Equation 3, and thus, image smoothing is achieved.

$$G(x,y)=(\tfrac{1}{2}\pi\sigma^2)\square\exp(-(x^2+y^2)/2\sigma^2) \qquad \text{(Equation 2)}$$

$$F(x,y)=G(x,y)\square f(x,y)=\square G(x+u,\ y+v)\square f(x,y)dudv\ \square$$
shows convolution. (Equation 3)

Further, in another example, it is also possible to eliminate noise regularly occurring by use of the Fourier transform.

Next, the degraded image is restored by eliminating the noise (step 282). By way of example the degraded image is restored by the Wiener filter. The Wiener filter gives such an image that a mean square error between an image f(x, y) after input and an image f'(x, y) after restoration becomes smallest.

Moreover, a check is made as to whether or not there is a large difference in appearance between the detected image 280 to be compared and the reference image 280'. Examples of evaluation indicators for this check include feature indices such as contrast, dispersion (standard deviation) of brightness, and frequencies of noise components. These feature indices are calculated between the images (step 283), and the calculated feature indices are then compared between the images (step 284). If there is a large difference, then the images are corrected so that these feature indices become closer (step 285). The above-mentioned Wiener filter may also be used between the detected image 280 and the reference image 280'. In addition, in detection processing, a judgment is made as to whether or not sensitivity is decreased (step 286). If it is judged that the sensitivity is at a level at which the feature indices cannot be corrected, the sensitivity is decreased in the comparing unit 205 so as to prevent a false report from occurring.

Incidentally, a detailed defect calculation method used in the image processing unit 50 can be realized by the method described in Japanese Patent Laid-open No. 2001-194323, or the like.

Next, the illumination light source 3 will be described. In order to achieve higher resolution, it is necessary to shorten the wavelength. Therefore, it is probable that as a means for providing illumination with high luminance in an ultraviolet wavelength band where its effect is best produced, it is desirable to adopt laser light as a light source. As described above, adopting ultraviolet laser light as a light source brings a great advantage. Thus, according to the present invention, an illumination method using the ultraviolet laser light will be described.

Figure 5:
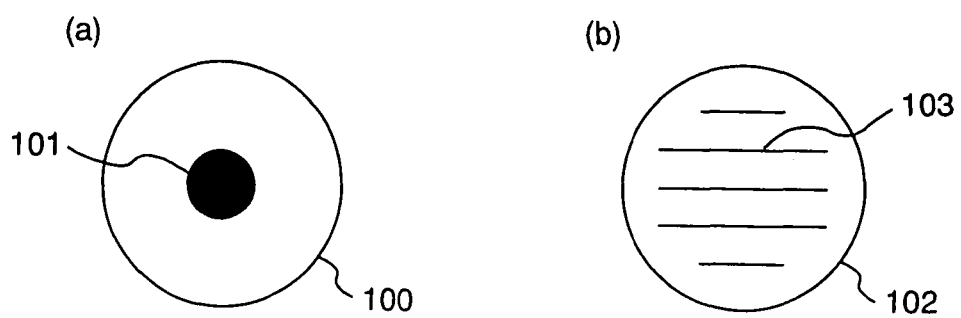
FIG. 5 is diagrams illustrating an illuminated state on a pupil of a detection objective lens, and an illuminated state on a visual field, when they are illuminated by an electric discharge tube.

FIGS. 5(*a*), 5(*b*) are diagrams illustrating an illuminated state of the pupil of the objective lens 20 and an illuminated state of a visual field respectively in the case where they are irradiated with usual white light. At a position of the pupil 100, an image 101 of the light source is formed. At a position of a visual field 102, the whole visual field 103 is substantially evenly irradiated.

Figure 6:
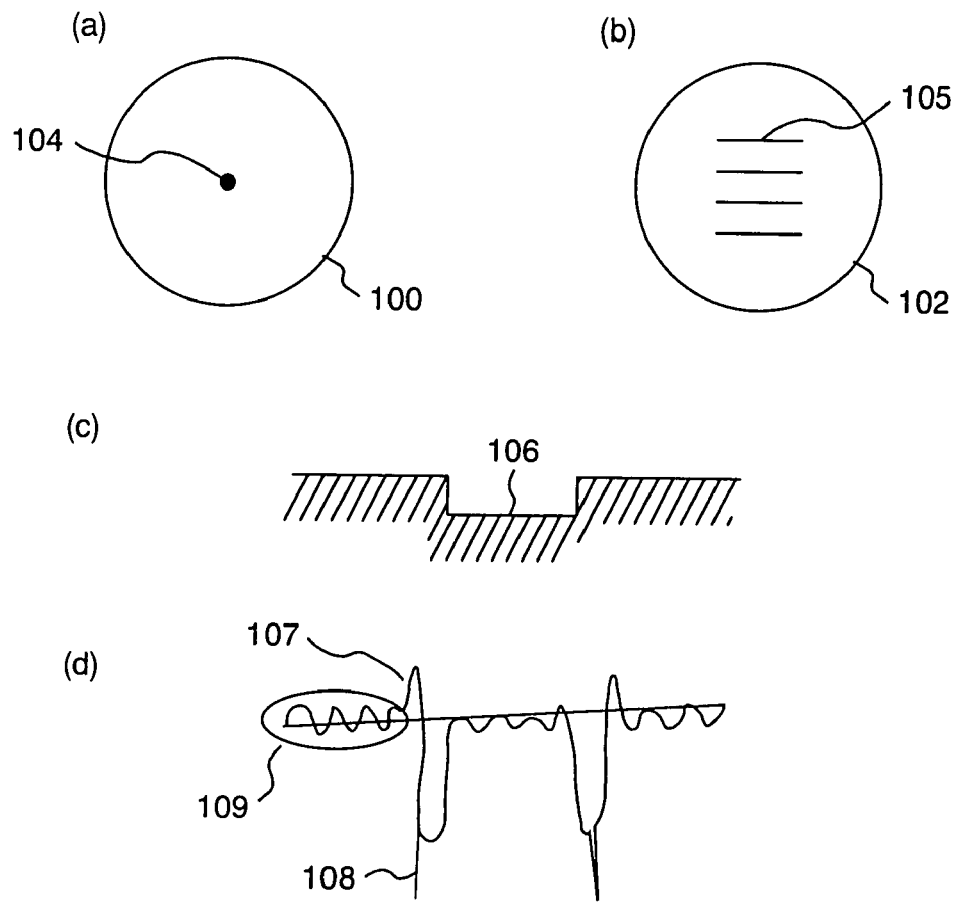
FIG. 6 is diagrams illustrating an illuminated state on the pupil of the detection objective lens, and an illuminated state on a visual field, when they are illuminated with laser light, and also illustrating a pattern on the visual field, and a detection signal obtained therefrom.

Next, FIG. 6 is diagrams illustrating a case where they are irradiated by a laser light source. In a similar manner, FIG. 6(*a*) illustrates a pupil; and FIG. 6(*b*) illustrates a visual field. In the case of laser light, because the light source forms a small spot, a light source image 104 at the pupil 100 shown in FIG. 6(*a*) becomes a point. In the visual field 102 shown in FIG. 6(*b*), only the center of the visual field is irradiated (105). For example, in the case of a pattern 106 having a cross section as shown in FIG. 6(*c*), an image having a detection waveform as shown in FIG. 6(*d*) is formed. Thus, when irradiating the circuit pattern 106 with a laser beam to obtain an image of a circuit pattern, overshoot 107 or undershoot 108 occurs at an edge part, or a speckle 109 occurs. Its cause is because C of the radiation is small. This means that the visual field below the objective lens 20 is not irradiated from various angles. When illuminating with usual white light, illumination with a certain magnitude is performed on the pupil, and illumination is performed on the visual field from a direction having an angular range equivalent to NA (numerical aperture) of the objective lens.

Figure 7:
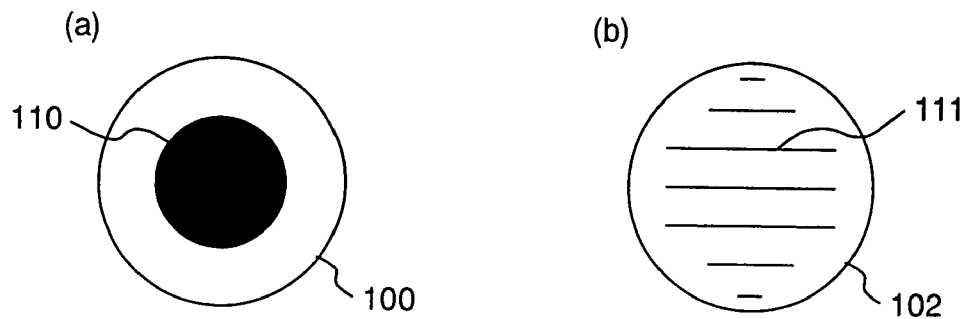
FIG. 7 is diagrams illustrating an illuminated state on the pupil of the detection objective lens, and an illuminated state on a visual field, when they are illuminated with laser light with the pupil being opened.

In the case of light having coherence like a laser beam, $\sigma$ becomes 0 (it is proportional to the magnitude of the light source on the pupil). This is because a light source image of the light having coherence is a point and accordingly an image on the pupil 100 becomes a point. As a matter of course, the whole area 111 of the visual field 102 can be substantially evenly irradiated as shown in FIG. 7(*b*) by projecting on the pupil 100 the luminous flux 110 expanded by another lens system as shown in FIG. 7(*a*). However, because the laser beam itself involves coherence, the result brought is the same as a case where all light is emitted from a position of $\sigma=0$ (105 shown in FIG. 6(*b*)), which does not solve the problem. Accordingly, a means for reducing coherence of a laser beam is required. In order to reduce the coherence, it is needed only to reduce either time coherence or spatial coherence.

Figure 8:
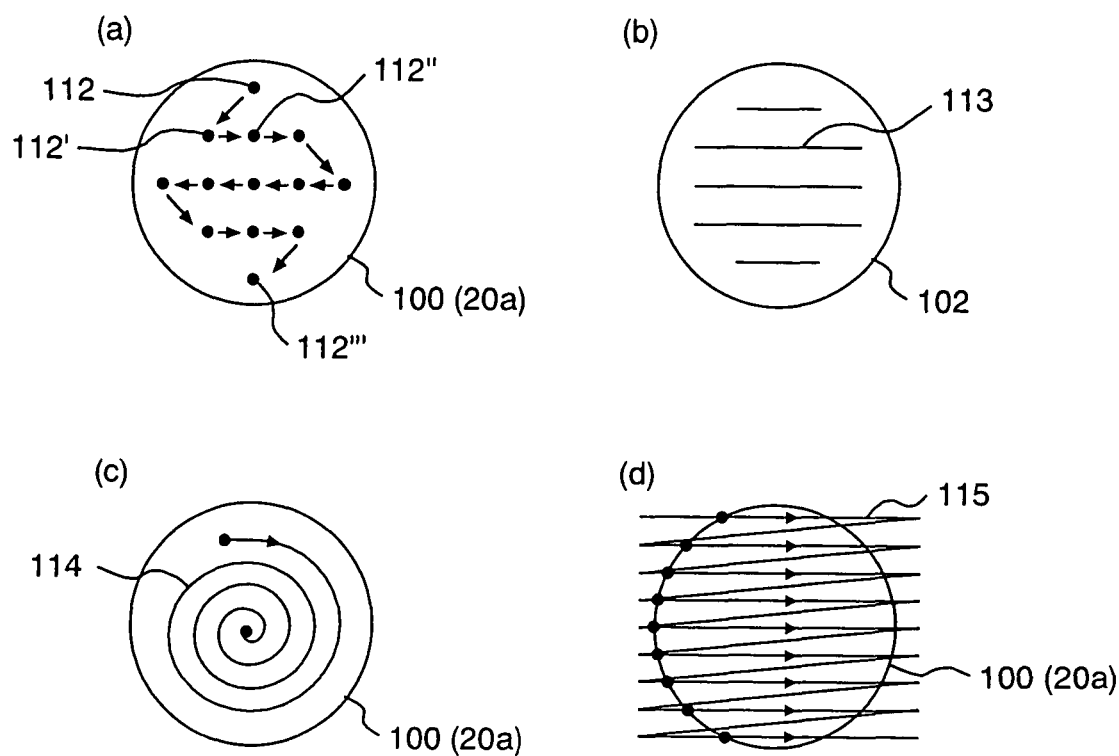
FIG. 8 is explanatory diagrams illustrating principles of coherence reduction by a coherence reduction optical system according to the present invention.

FIG. 8 is explanatory diagrams illustrating principles of coherence reduction by the coherence reduction optical system 17 of the apparatus according to the present invention. In FIG. 8(*a*), in the pupil 100 (20*a*) of the objective lens 20, a position 112 is first irradiated with illumination light, next a position 112' is irradiated, next a position 112'' is irradiated, . . . and lastly a position 112''' is irradiated, which is how the pupil 20*a* is scanned. Consequently, a visual field 102 shown in FIG. 8(*b*) becomes illumination 113. This produces the same effects as those produced by the illumination of usual white light described with reference to FIG. 5.

In addition, as shown in FIG. 8(*c*), scanning may also be performed spirally (114) in the pupil 100. Moreover, as shown in FIG. 8(*d*), scanning may also be performed two-dimensionally (115) in the pupil 100. During the scanning, a speckle, and overshoot and undershoot images are obtained at each position. However, there is no coherence across them because the time at which they are obtained differ from one another. Accordingly, adding up or integrating them in the image sensor 21 makes it possible to obtain an image which is the same as that obtained by an incoherent light source. With the object of adding up or integrating them in the image sensor 21, the image sensor 21 has a pixel size of about 0.05 to 0.3 μm in terms of a sample (visual field). Accordingly, a detector of accumulated type (more specifically, TDI sensor) such as a CCD is suitable. In other words, one-dimensional sensor is used as an accumulated type image sensor.

Figure 9:
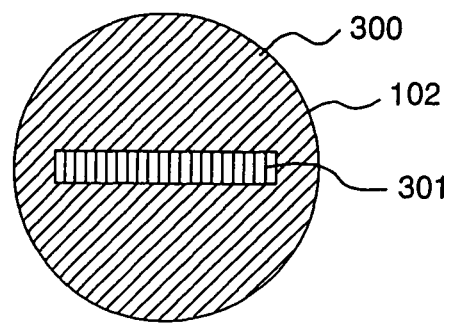
FIG. 9 is a diagram illustrating the relationship between a detection range of an image sensor on a visual field and an illumination area according to the present invention.
Figure 10:
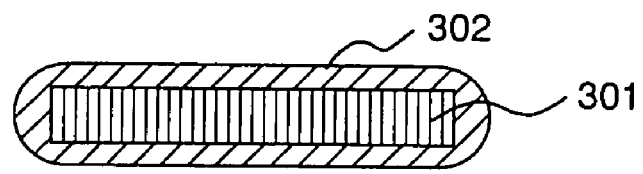
FIG. 10 is a diagram illustrating the relationship between a detection range of an image sensor on a visual field and an illumination area according to the present invention.

As shown in FIG. 9, if a one-dimensional sensor is used as the image sensor 21, even when the entire surface of the visual field 102 is irradiated, an illuminated area that contributes to detection is only an area 301. Therefore, in an area 300 occupying a large part of the other light power, no contribution is made to the detection. For this reason, in order to increase illuminance, as shown in FIG. 10, it is desirable to linearly irradiate the one-dimensional sensor as illustrated in an area 302. According to the present invention, among various kinds of CCD sensors as accumulated type, a time delay and integration type sensor, i.e., a TDI (Time Delay & Integration) sensor, is adopted as the image sensor 21. In the case of the TDI sensor, in the lateral direction, N-step (about from several tens to 256 steps, or about 1000 steps) light receiving elements called stage are arrayed on the visual field, and in the longitudinal direction, the plurality of stages being arrayed form a single sensor.

Figure 11:
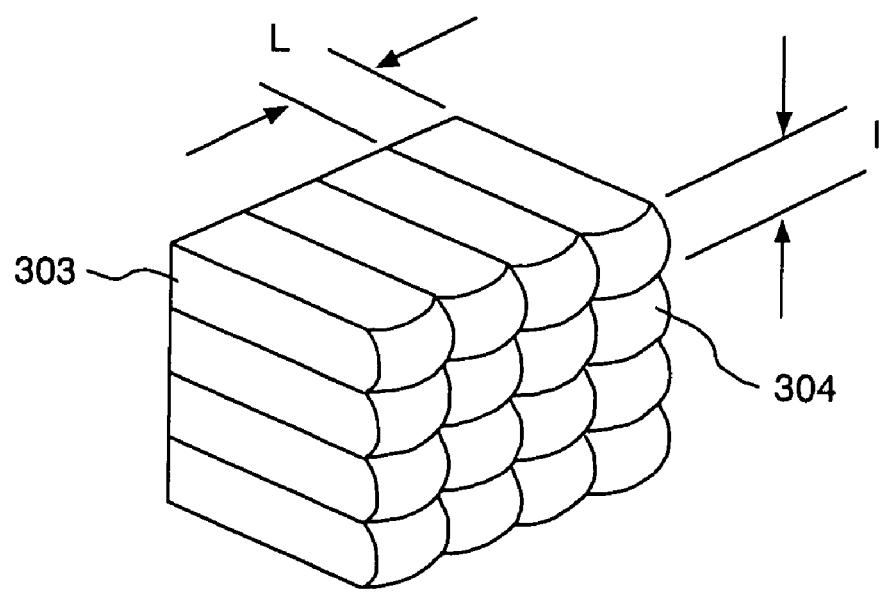
FIG. 11 is an explanatory diagram illustrating a homogenizer for illumination according to the present invention.

Next, the illumination-range formation optical unit 14 will be specifically described with reference to FIG. 11. As shown in FIG. 11, it is possible to achieve illumination in a rectangular form by using a homogenizer 303 for the illumination-range formation optical unit 14 after the beam expander 13 that performs emission. The homogenizer 303 is formed by placing a plurality of rectangular lens arrays 304. The difference between a long side L and a short side l enables the illumination in a rectangular form. If L=1, the illumination becomes circular. Incidentally, it becomes possible to change an illumination range of the rectangle on the sample by changing, both in the long side and short side directions, pitches of the lens array 304 forming second order point light sources. In this manner, placing the plurality (great number) of lens arrays 304 makes it possible to realize a plurality (great number) of secondary point light sources on the pupil. Accordingly, it is possible to eliminate irregularities in illumination for the sample.

Next, the ND filter 11 for limiting the quantity of light will be specifically described with reference to FIGS. 12(*a*) and 12(*b*). FIG. 12(*a*) is a diagram illustrating where the ND filter 11 is placed; and FIG. 12(*b*) is a diagram illustrating the relationship between a rotating angle of the ND filter 11 and its transmittance. For the purpose of stabilization of the laser light source, the luminous flux L1 coming from the laser light source 3 is emitted with maximum output. Because of it, it is necessary to limit the quantity of light reaching the image sensor 21. In FIG. 12(*a*), the luminous flux coming from the laser light source 3 is reflected by the mirrors 6, 7, and then passes through the ND filter 11. At this time, if the ND filter 11 is perpendicular to the luminous flux, its reflected light is reflected by the mirrors 6, 7 again, and eventually returns to the inside of the laser light source 3. Just then, the laser beam interferes with its reflected light in a resonator of the laser light source 3, causing a laser output to become unstable. An optical axis of the ND filter 11, therefore, is tilted only by angle α relative to the luminous flux. More specifically, it is desirable to set the angle α at such a value that the luminous flux R reflected by an incident plane of the ND filter 11 does not directly return to a laser emission opening of the laser light source 3. As the ND filter 11, for example, there is used a filter whose transmittance varies with rotating angle as shown in FIG. 12(b). Incidentally, the ND filter 11 can rotate in directions indicated by arrows, and can also be fixed at a given rotating angle by the ND filter control circuit 12.

Figure 13:
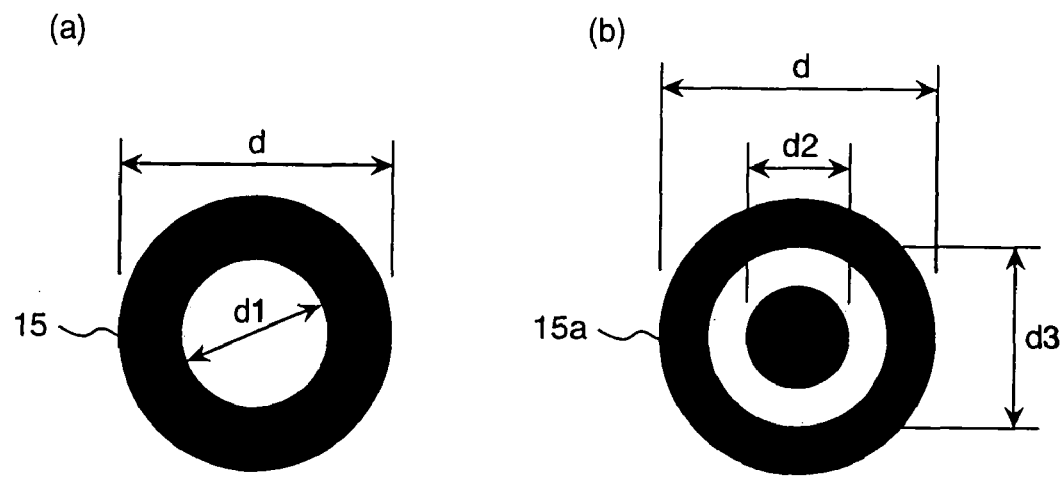
FIG. 13 is explanatory diagrams illustrating an embodiment of an aperture diaphragm according to the present invention.

Next, the aperture diaphragm system 15 will be specifically described with reference to FIG. 13. FIG. 13(a) illustrates one embodiment of the aperture diaphragm 15 according to the present invention. The aperture diaphragm 15 can change a diameter d1 through which the luminous flux passes. Symbol d is the same as a diameter of the pupil 20a of the objective lens 20, and d1=d corresponds to illumination sigma 1. A position of the aperture diaphragm 15 is a position conjugated with a position of the pupil 20a of the objective lens, and changes illumination sigma. In accordance with a surface profile of the sample 1 which is set as an inspection recipe or a review recipe, the CPU 121 of the main-body control circuit 50 can arbitrarily set the diameter d1 of the aperture diaphragm 15 through the aperture-diaphragm control circuit 16. In addition, it is also possible to form the aperture diaphragm 15 in an orbicular shape (including a pseudo orbicular shape). FIG. 13(b) illustrates the aperture diaphragm 15a at the time of realizing orbicular illumination. Here, a combination of inside sigma d2 and outside sigma d3 can be freely made. Using these in combination enables detection with higher resolution.

Figure 14:
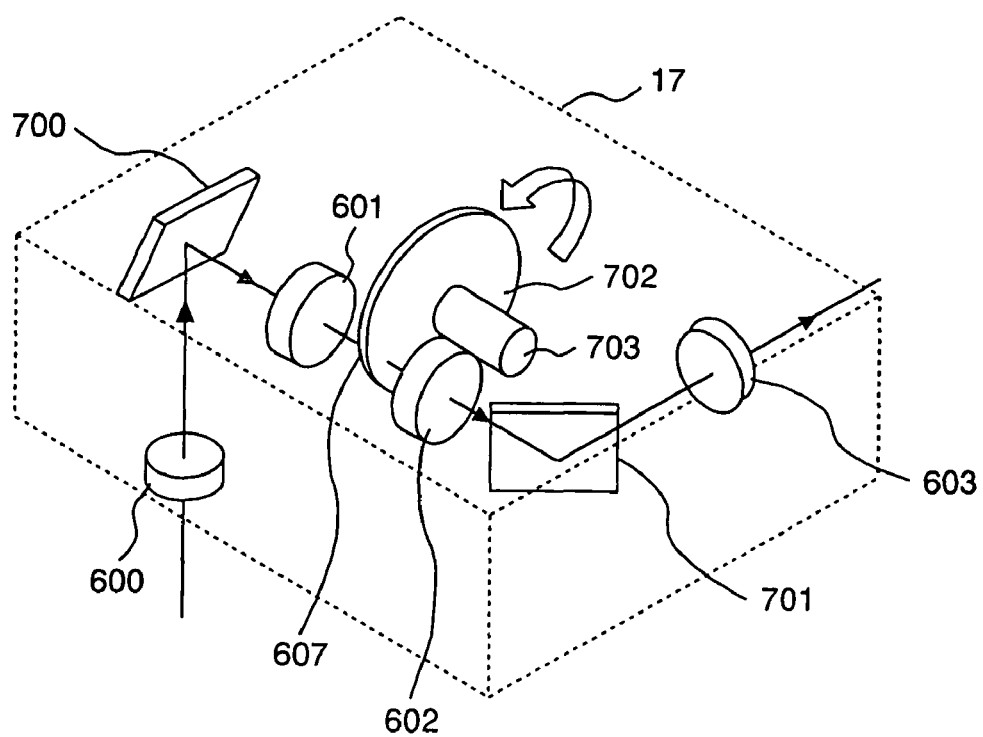
FIG. 14 is an explanatory diagram illustrating a first embodiment in which spatial coherence of laser illumination is reduced in a coherence reduction optical system according to the present invention.
Figure 15:
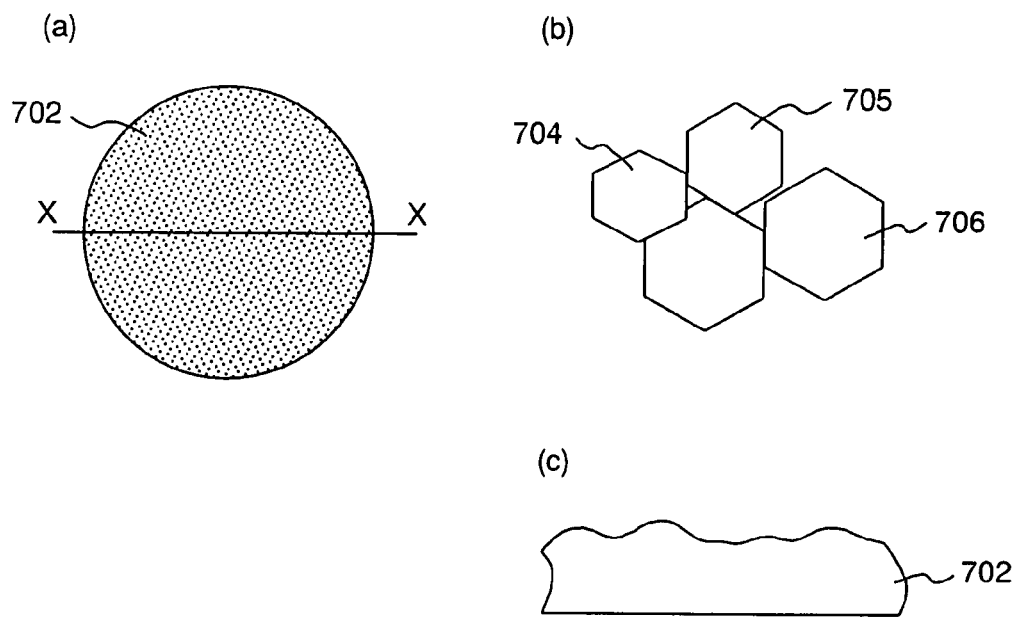
FIG. 15 is diagrams each illustrating a shape of a diffusing plate according to the present invention.

Next, a first embodiment of the coherence reduction optical system 17 will be described with reference to FIGS. 14 through 16. In the first embodiment, a reduction in coherence is achieved by using a method in which a diffusing plate 702 for scattering illumination light is provided in an optical path of a laser beam. As shown in FIG. 14, the coherence reduction optical system 17 has a configuration in which a point light source group in the illumination-range formation optical unit 14 is imaged on the pupil 20a of the objective lens 20 by use of lenses 600, 601, 602, 603, and in which the diffusing plate 702 is inserted into an optical path between the lens 601 and the lens 602. The diffusing plate 702 can be rotated by a motor 703. The diffusing plate 702 is placed at a position 607 conjugated with the sample 1. Incidentally, each of reference numerals 700, 701 denotes a mirror. FIG. 15 is diagrams each illustrating a shape of the diffusing plate 702.

FIG. 15(a) is a front view; and FIG. 15(b) is a detailed view illustrating a diffusing surface. FIG. 15(c) is a cross section taken along line X-X in FIG. 15(a). It is desirable that the diffusing plate 702 is formed by placing particulates 704, 705, 706 at random. Viewing from a surface of the diffusing plate 702, each of the particulates 704, 705, 706 has a particle diameter of about 0.1 mm, and has a shape of a polygon or a circle. Moreover, it is desirable that with respect to the quantity of unevenness, the cross section also has a random shape in accordance with a particle diameter. By rotating this diffusing plate 702 at high speed within accumulation time of the image sensor 21, it is possible to scan (deflect) a large number of laser beams at random on the pupil 20a, and to completely eliminate light coherence.

A method for rotating the diffusing plate 702 at high speed can be achieved by adopting an air turbine motor as the motor 703; a rotating speed of several kHz can be achieved. However, when trying to achieve the rotating speed of several kHz, if the diffusing plate 702 and the motor 703 are not well secured, the eccentricity will occur to cause oscillations at the time of rotation, which incurs the possibility of exerting an influence on the accuracy of the apparatus itself. Therefore, there is proposed a method that can be realized at such low rotating speed that the rotating speed of the diffusing plate 702 is not required to reach the accumulation time of the image sensor 21.

Figure 16:
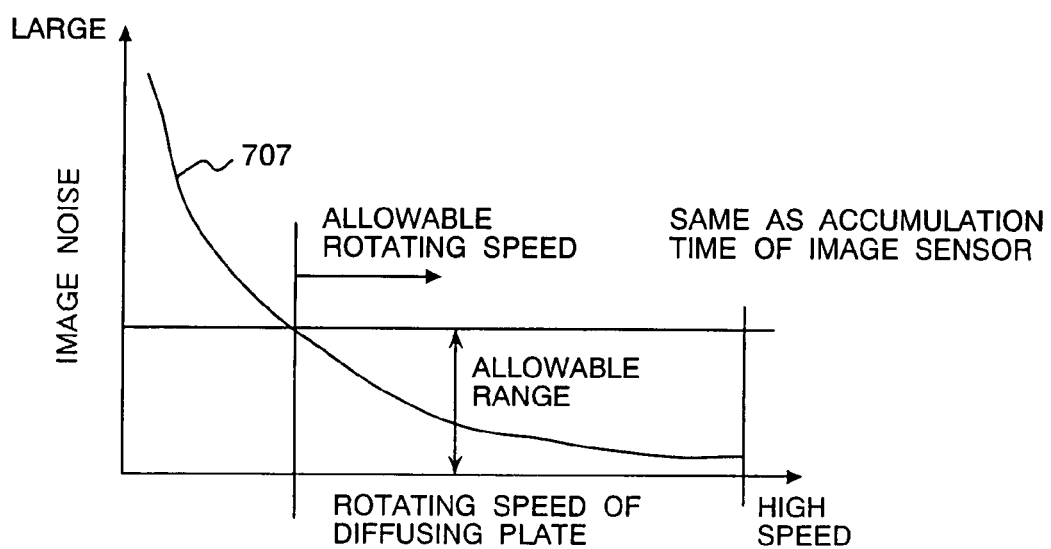
FIG. 16 is a chart illustrating the relationship between the rotating speed of the diffusing plate according to the present invention and the coherence (image noise)

FIG. 16 illustrates the relationship between the rotating speed of the diffusing plate 702 and image noise. A horizontal axis indicates the rotating speed of the diffusing plate 702, and rotation at higher speed is shown on the right side. A vertical axis indicates image noise, and larger noise is shown on the upper side. The image noise corresponds to coherence on the sample 1. An image is actually obtained by the image sensor 21. A waveform 707 is formed by measuring random noise at that time. If the coherence is large, it means that image noise becomes large. If the coherence is small, the coherence is sufficiently reduced. In FIG. 16, it is understood that with the increase in rotating speed of the diffusing plate 702, image noise becomes smaller. Because the image noise that is smaller than or equal to noise at the time of defect judgment is acceptable, it is needed only to set the rotating speed at a value within an allowable range. This rotating speed is about a quarter of the accumulation time of the image sensor 21.

Next, a second embodiment of the coherence reduction optical system 17 will be described with reference to FIG. 17. In this second embodiment, a rotating phase plate 750 is provided at the position where the diffusing plate 702 is placed in the first embodiment.

FIG. 17 is diagrams illustrating a configuration of the rotating phase plate 750. FIG. 17(a) is a front view; FIG. 17(b) is a detailed view; and FIG. 17(c) is a cross section taken along line X-X in FIG. 17 (a). At a position 751, the rotating phase plate has a thickness (λ) at which a phase does not change. Steps are made by shifting a phase, for example, by a phase difference (½λ) at a step 754, by a phase difference (¼λ) at a step 752, by a phase difference (¾λ) at a step 753, and so on. The large number of steps, each of which has a different depth, are provided at random. As shown in FIG. 14, instead of the diffusing plate 702, this rotating phase plate 750 is secured to the motor 703, and is thereby rotated. This permits phases of a large number of laser beams to be changed (to be phase modulated at random) in accordance with a depth of each step, which is equivalent to the operation being scanned on the pupil 20a of the objective lens 20. This makes it possible to reduce the coherence of the laser beams.

Further, FIG. 17(d) is a diagram illustrating an example in which a top surface of the step is not flat but projecting. Each top surface of projections is made in the following manner: at a position 751', the top surface has a height at which a phase does not change; at a step 754', it is shifted by a phase difference of ½λ; at a step 752', it is shifted by a phase difference of ¼λ; at a step 753', it is shifted by a phase difference of ¾λ; and so on. In a similar manner, a phase of a laser beam can be changed in accordance with a depth of each step. Accordingly, it is possible to reduce the coherence of the laser beam. In addition to it, since angles of the projections are different from one another, an effect of scattering the luminous flux is also produced, which enables further reduction in coherence.

Figure 18:
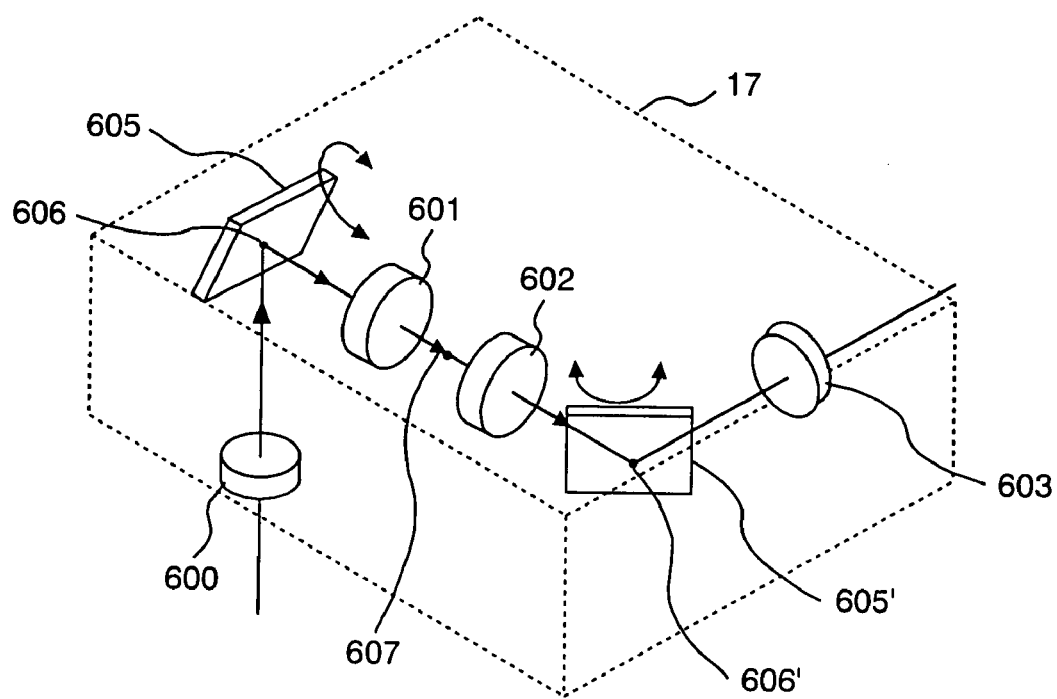
FIG. 18 is an explanatory diagram illustrating a second embodiment in which spatial coherence of laser illumination is reduced in a coherence reduction optical system according to the present invention.

A third embodiment of the coherence reduction optical system 17 will be described with reference to FIG. 18. This third embodiment uses a resonant galvanometer mirror as a means for scanning a light-source image. By use of the lens 600, the luminous flux coming from the illumination light source 3 is provided at a position 606 conjugated with the pupil 20a of the objective lens 20. Moreover, by use of the lenses 601 and 602, reflected light is provided at the next conjugate position 606'. An image of this reflected light is formed in the pupil 20a of the objective lens 20 by use of the lens 603. A galvanometer mirror a 605 capable of turning in up and down directions is placed at this conjugate position 606; and a galvanometer mirror b 605' capable of turning in right and left directions is placed at the conjugate position 606'. Incidentally, the sample 1 and the conjugate position 607 are provided between the lens 601 and the lens 602.

Figure 19:
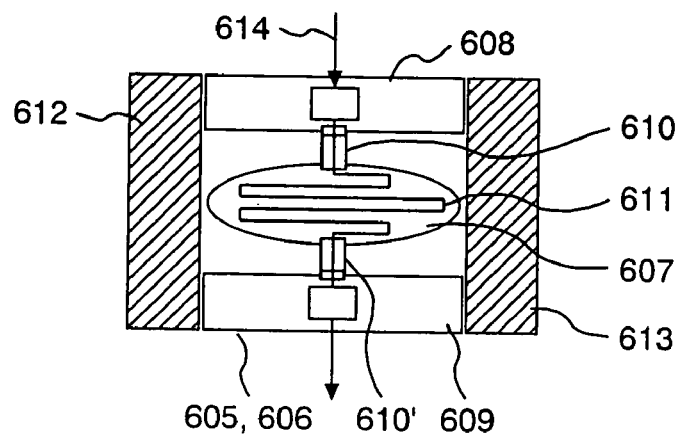
FIG. 19 is an explanatory diagram illustrating a resonant mirror according to the present invention.

Next, another embodiment of the resonant galvanometer mirror is shown in FIG. 19. As shown in FIG. 19, each of the galvanometer mirrors 605, 605' is made by shaping a fixed part and a turning part into one unit. To be more specific, a turning surface 607 is formed by bars 610, 610' that stretch from fixed sides 608, 609 respectively. A coil 611 is formed on the front side of the surface 607. There are provided magnets 612, 613 on both ends of the coil 611. It is so devised that when an electric current 614 is applied to the coil 611, the coil 611 repels the magnets 612, 613, causing the surface 607 to turn about the bars 610, 610'. It is to be noted that coating which totally reflects a laser beam is provided on the backside of the surface 607, which serves as a mirror.

Figure 20:
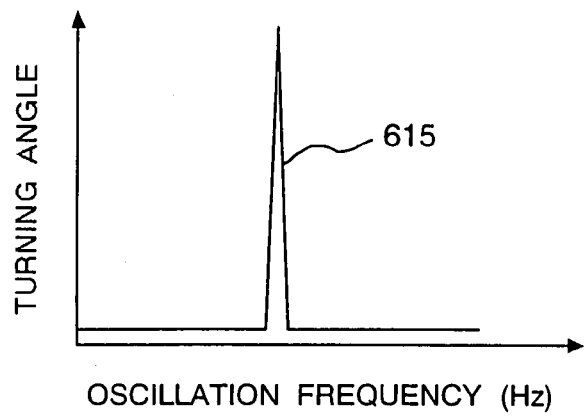
FIG. 20 is a chart illustrating properties of the resonant mirror according to the present invention.
Figure 21:
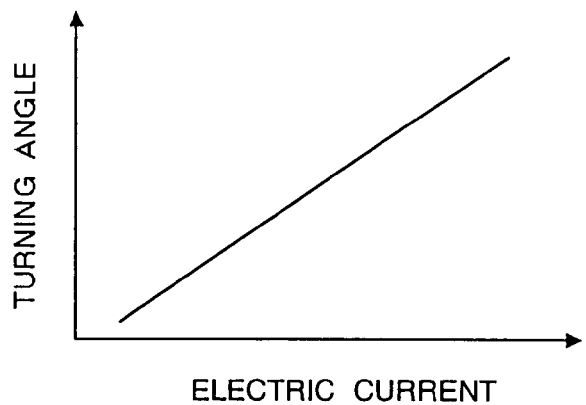
FIG. 21 is a chart illustrating properties of the resonant mirror according to the present invention.

It is confirmed that when applying a constant electric current, the surface 607 having a mirror surface on the backside turns at a constant frequency. FIG. 20 illustrates frequency characteristics. The horizontal axis indicates a resonance frequency, and the vertical axis indicates a turning angle. A frequency having a peak is arbitrarily given within a range from 1000 to 5000 Hz. This frequency can be controlled by changing widths of the above-mentioned bars 610, 610'. As a matter of course, a frequency of 1000 Hz or less can also be used. The galvanometer mirrors are produced with such properties that the turning angle becomes maximum at a given frequency. FIG. 21 illustrates the relationship between a current value and a turning angle. The horizontal axis indicates an electric current, and the vertical axis indicates a turning angle. In accordance with an applied electric current, the turning angle can also be limited. Since the galvanometer mirror which is placed as shown in FIG. 18 operates the luminous flux up and down, and right and left, it is desirable to place a galvanometer mirror having the same resonance frequency as shown in FIG. 19.

Incidentally, it is desirable that the resonance frequency of the galvanometer mirror be synchronized with the accumulation time of the image sensor 21. The time taken by the image sensor 21 to obtain an image is determined as the product of a drive frequency and the step number of stages in the lateral direction. For example, if the drive frequency is 300 kHz and the step number of stages is 500 steps, an image is obtained at 600 Hz. If the properties are set so that the frequency of the resonant galvanometer mirror capable of turning becomes 600 Hz, one turning motion can be achieved in the accumulation time. Otherwise, if the resonant galvanometer mirror has a frequency which differs from an ideal frequency (for example, 611 Hz, or the like) due to unevenness at the time of the production or other causes, changing the drive frequency of the image sensor 21 to, for example, 305.5 kHz permits one turning motion to be achieved in the accumulation time. That is, adjusting either the image obtaining time of the image sensor or the frequency of the resonant galvanometer mirror enables ideal turning and ideal image obtaining.

Figure 22:
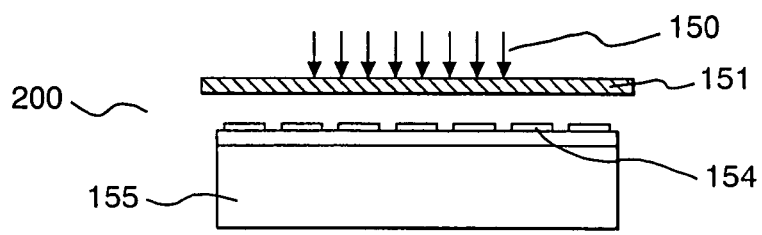
FIG. 22 is a diagram illustrating a surface irradiation TDI image sensor.

Next, an embodiment of a TDI sensor which is adopted as the image sensor 21 capable of detecting UV light, in particular DUV light, will be described. FIG. 22 is a diagram illustrating a surface reflection sensor. If a DUV laser light source is used as the illumination light source 3, it is necessary to use an image sensor having the sensitivity to DUV. Since incident light 150 passes through a cover glass plate 151 and then enters a CCD 155 through a gate 154, incident light with a shorter wavelength damps. Accordingly, a surface irradiation image sensor 200 has little sensitivity to a wavelength of 400 nm or less, and therefore cannot detect DUV light effectively.

Figure 23:
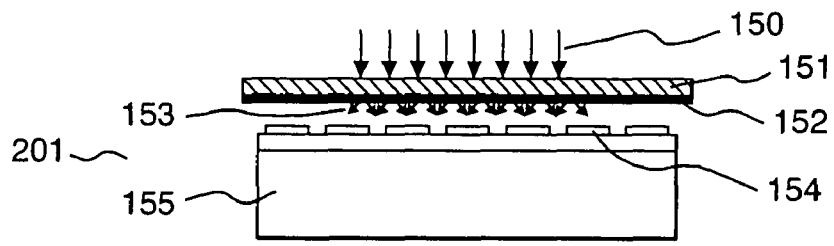
FIG. 23 is a diagram illustrating a surface irradiation TDI image sensor according to the present invention.
Figure 24:
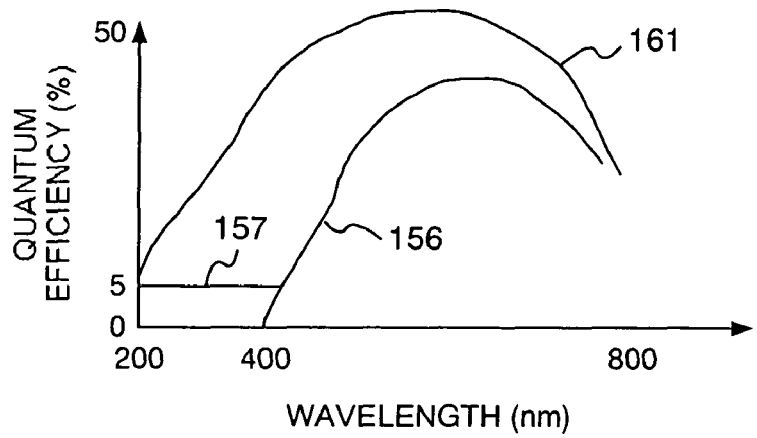
FIG. 24 is a chart illustrating properties of a TDI image sensor according to the present invention.

For this reason, there is a method whereby DUV light is detected using an image sensor having the sensitivity only to visible light. In this method, organic thin film coating is provided on a cover glass plate; and when DUV light is entered, visible light is emitted in response to the DUV light, and thereby the DUV light is detected. FIG. 23 is a diagram illustrating an image sensor that adopts the organic thin film coating method. In an image sensor 201 adopting the organic thin film coating method, an organic thin film coating 152 is provided on a cover glass plate 151 so that transmitted light of incident light 150 causes fluorescence 153 to be emitted from an organic thin film coating surface 152. Accordingly, even the surface irradiation image sensor with the sensitivity only to visible light can detect DUV light. FIG. 24 illustrates its spectral characteristics. Spectral characteristics 156 are characteristics of the usual surface irradiation image sensor 200. The sensor has no sensitivity to a wavelength of 400 nm or less. Spectral characteristics 157 are characteristics of the image sensor 201 adopting the organic thin film coating method. The sensitivity to a wavelength of 400 nm or less is added.

Figure 25:
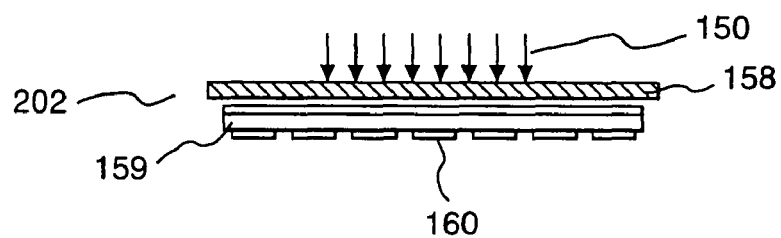
FIG. 25 is a diagram illustrating a backside irradiation TDI image sensor according to the present invention.

In order to further improve the sensitivity to DUV light, using a backside irradiation image sensor suffices. FIG. 25 is a diagram illustrating a structure of the backside irradiation image sensor. The backside irradiation image sensor 202 is devised to pass the incident light 150 through a cover glass 158. Then, light enters a CCD through a thin backside 159 having no gate structure. No light, therefore, passes through a gate 160. Accordingly, as shown in FIG. 24, the spectral characteristics 161 are obtained, resulting in high quantum efficiency (for example, 30% or more) and a large dynamic range (for example, 3000 or more) as well as the sensitivity to a wavelength of 400 nm or less. The backside illumination image sensor is particularly advantageous for illumination with a shorter wavelength less than 200 nm. In the case of such an image sensor, even when using some illumination wavelengths, one image sensor can handle the wavelengths. In addition, use of a TDI (Time Delay Integration) image sensor makes it possible to enhance the sensitivity. Moreover, by providing antiblooming characteristics, it is possible to solve the problem that when the quantity of detected light that has been obtained is larger than required, electric charges overflow into circumferential pixels. Thus, it is desirable to use an image sensor having the highest quantum efficiency for a wavelength at the time of inspection.

Moreover, in addition to making the resolution higher by ultraviolet light, as described above, by controlling the polarization element group 19 so as to filter the frequency from the sample using the unillustrated method, it is also possible to improve the contrast of a pattern imaged by the image sensor 21. Paying attention to the fact that in order to improve the pattern contrast, it is possible to freely control a polarized state of ultraviolet laser light by controlling the polarization element group 19, the image sensor 21 can detect a part of a polarized component of detected light by controlling a direction and ellipticity of polarization of illumination light. Characteristics of illumination by ultraviolet laser light include single wavelength, and linear polarization. Therefore, configuring the polarization element group 19 provided in an optical path as a half-wave plate and a quarter-wave plate allows its polarized state to be controlled with high efficiency. The control is performed by, for example, rotating the half-wave plate and the quarter-wave plate about an optical axis. Depending on a shape of the sample, the pattern contrast largely changes by the polarized state of illumination. Accordingly, making the polarized state controllable (rotating a wave plate for positioning) enables improvement in performance of the optical system. To be more specific, a direction of linear polarization can be controlled by the half-wave plate of the polarization element group 19; and the ellipticity can be changed by the quarter-wave plate. This enables improvement in sensitivity. These combinations can realize both parallel Nicols and crossed Nicols. As a matter of course, a circular polarization state can also be achieved. It is to be noted that these do not depend on an illumination wavelength itself.

In addition, so long as the above-mentioned concept holds true, any configuration for embodying the concept may be arbitrarily adopted. As a matter of course, a spatial filter may also be placed at a position conjugated with the pupil 20a of the objective lens 20 to attenuate zero-order light (it is also possible to lead scattered light coming from a foreign material to the image sensor by blocking diffracted light coming from a pattern using the spatial filter). However, high-order diffracted light can be extracted with higher efficiency by controlling polarized light. According to the experiments by the inventors, it is found out that the contrast is improved by about 20 to 300%.

Next, an embodiment of attenuating zero-order light will be described. FIG. 26 is diagrams each illustrating an embodiment of a detection diaphragm 30. The detection diaphragm 30 is used to limit the pupil 20a at the time of detecting the objective lens 20.

FIG. 26(*a*) is a general view illustrating the detection diaphragm 30. Symbol D is equivalent to the size of the pupil 20a. Each of an outside diaphragm D1 and an inside diaphragm D2 can be changed in size by an unillustrated method.

FIG. 26(*b*) illustrates a usual state in which the outside diaphragm D1 is released at the maximum while the inside diaphragm D2 is eliminated. In this state, the luminous flux in the pupil 20a can be totally detected.

FIG. 26(*c*) illustrates a state in which the outside diaphragm D1 is released at the maximum while the inside diaphragm D2 is set at 30'. This makes it possible to limit the quantity of light in the central part of the pupil 20a. In other words, this corresponds to the attenuation of zero-order light as described above.

FIG. 26(*d*) illustrates a state in which the outside diaphragm D1 is set at 30" while the inside diaphragm D2 is eliminated. This makes it possible to limit the quantity of light in the circumferential part of the pupil 20a, and thereby to create the same state as that in which NA (σ) of the objective lens 20 is limited. Since this decreases the resolution, there is produced an effect of suppressing spot-like reflected light coming from the sample 1, that is to say, something called grain that is generated when detecting the sample 1 on which wiring is formed. In other words, since the spot-like reflected light often generates high-order diffracted light, an influence of the grain can be excluded so long as the high-order diffracted light is not detected. If the resolution is decreased, the high-order diffracted light is not detected. Accordingly, setting the detection pupil 30 to a state as shown in FIG. 26(*d*) effective.

Figure 29:
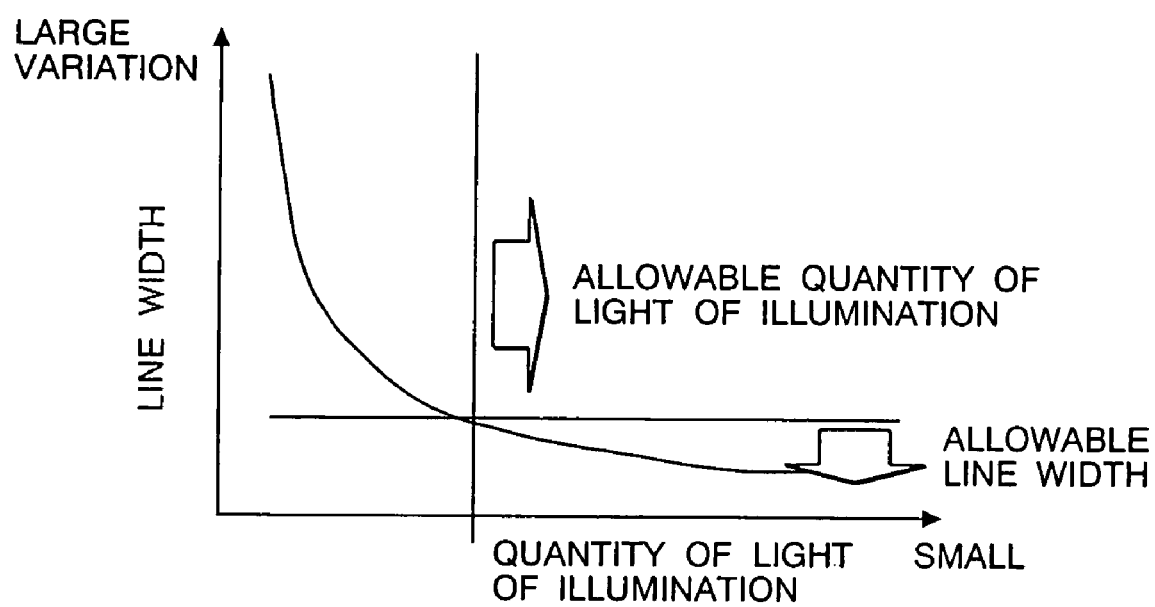
FIG. 29 is a chart illustrating the quantity of illumination light and a change in line width of a sample according to the present invention.

Operation in the above-mentioned configuration will be described. FIG. 29 illustrates an example of a change in line width at the time of inspection in a case where the sample is formed by resist. The horizontal axis indicates the quantity of illumination light at the time of inspection; and the smaller quantity of illumination light is shown on the right side. The vertical axis indicates a change in line width of the sample; and a larger change in line width is shown on the upper side. For the sample having such properties that are inputted into the CPU 212 and are then set as an inspection recipe, it is possible to perform inspection, which exerts no influence on the sample, first by calculating the quantity of transmitted light of the ND filter 11 using the CPU 212, and then by controlling the ND filter 11 using for example the ND filter control circuit 12 on the basis of the calculated quantity of transmitted light to perform inspection using the quantity of illumination light that is smaller than a permissible value of the change in line width.

In addition, it is probable that there are similar properties not only for resist but also for a sample (which is inputted into the CPU 212 and is then set as an inspection recipe) formed by a thin film, a metal film, etc., which is thought to exert an influence on the quantity of illumination light, a line width, or a surface profile. Therefore, for example, controlling the ND filter 11 to perform inspection for them using the quantity of illumination light, which is smaller than a permissible value of the change, makes it possible to perform inspection that exerts no influence on the sample. For this purpose, it is desirable that the CPU 212 of the main-body control circuit 50 controls the quantity-of-light adjusting unit 11, 4 so that the sample is not irradiated with illumination light more than necessary at the time of inspection.

Moreover, also in the optical system (in particular, in the illumination optical system), there is a possibility that the transmission of light will damage optical components or the sample. Therefore, in the main-body control circuit 50, on the basis of inspection conditions and review conditions which have been set in recipe setting screens 3300a, 3300b constituting a recipe setting unit shown in FIGS. 33 and 34, it is desirable to control the shutter 4 by use of the driving control circuit 5 according to an instruction from the CPU 212 so that the shutter 4 opens only during capturing an image both at the time of inspection and at the time of review.

Figure 30:
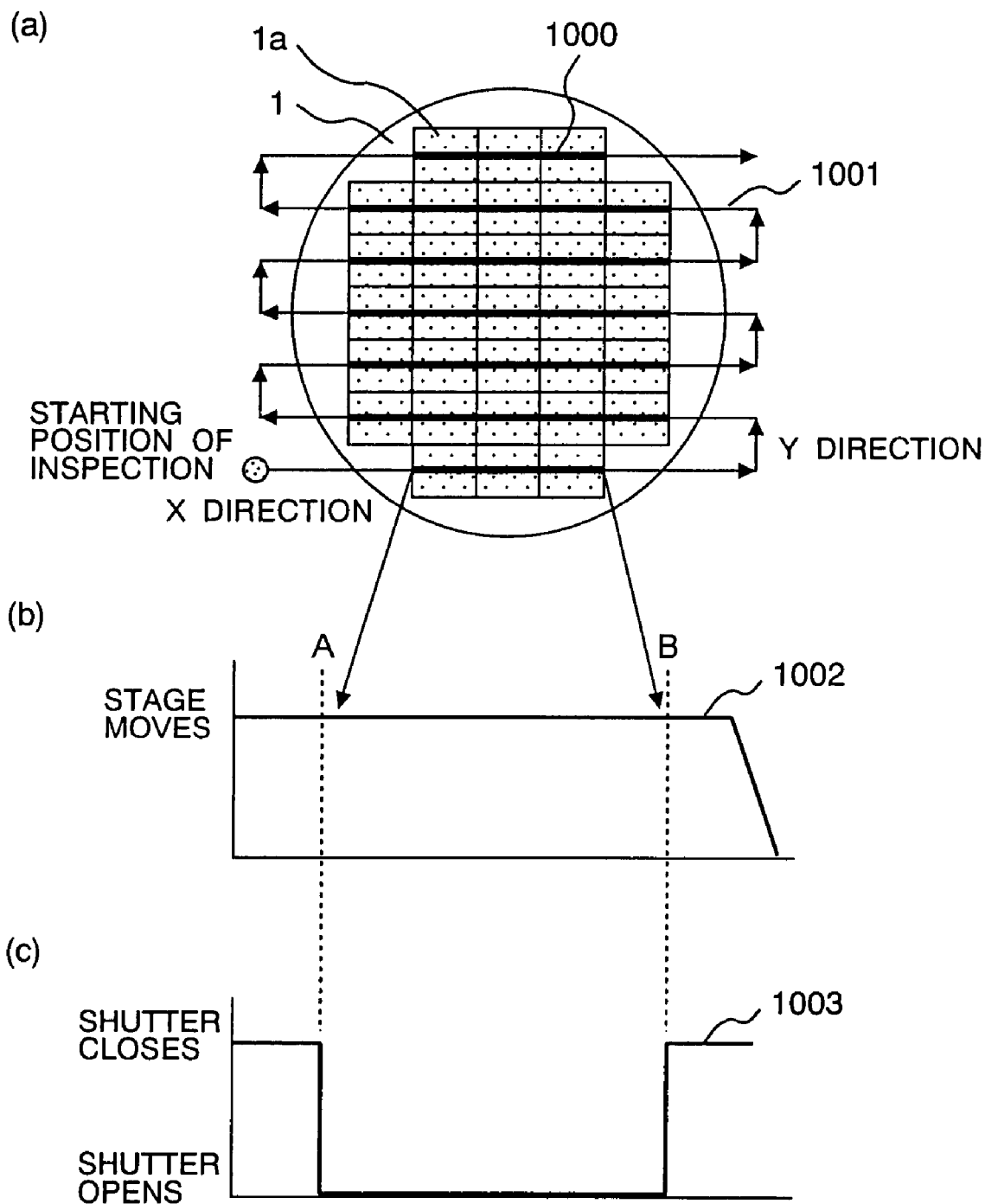
FIG. 30 is diagrams illustrating moves of a stage, and opening and closing of a shutter, at the time of inspection according to the present invention.

FIG. 30 illustrates one embodiment showing the relationship between irradiation of illumination light and inspection, which is based on array data of a chip determined by design data in accordance with a kind of a sample (semiconductor device) set by the recipe setting unit.

FIG. 30(*a*) is a diagram illustrating a shape of the sample (array data of a chip). Here, a pattern 1a is drawn on the sample 1. This pattern part 1a is inspected on the basis of an image signal detected by the image sensor 21. FIG. 30(*b*) illustrates a move pattern of a stage 2 in the X direction. This is based on the assumption that an inspection direction is the X direction, and that a direction of moving to the next inspection area is the Y direction.

FIG. 30(*c*) illustrates an example of the opening and closing pattern of the shutter 4. In the figure, a move is made from an inspection starting position in the X direction on the stage 2. The main-body control circuit 50 gives a starting position A of the pattern 1a to a shutter drive circuit (shutter control circuit) 5, and then moves the shutter 4 to the open side so that the sample 1 is irradiated with light of the light source 3. The stage control circuit 35 moves the stage 2 in the X direction according to an instruction from the main-body control circuit 50. As soon as the stage 2 reaches an ending position B of the pattern 1a, the driving control circuit 5 moves the shutter 4 including an optical deflector to the close side so that the sample 1 is not irradiated with light of the light source 3. Next, according to an instruction from the main-body control circuit 50, the stage is moved in the Y direction to inspect the next column. After that, the stage is moved in the X direction to the starting position of the pattern 1a where the opening and closing operation of the shutter 4 is performed in like manner. The shutter 4 is opened in a part 1000 drawn with a bold line in FIG. 30(a), whereas the shutter 4 is closed in a part 1001 drawn with a thin line. Such shutter operation according to an instruction from the main-body control circuit 50 prevents light from passing through a required part of the optical system (in particular, the illumination optical system). Accordingly, it is possible to reduce the damage of the optical system to a required minimum. More specifically, when closing the shutter 4, it is not necessary to intercept the light completely. It is needed only to remarkably reduce the quantity of irradiated light.

Figure 31:
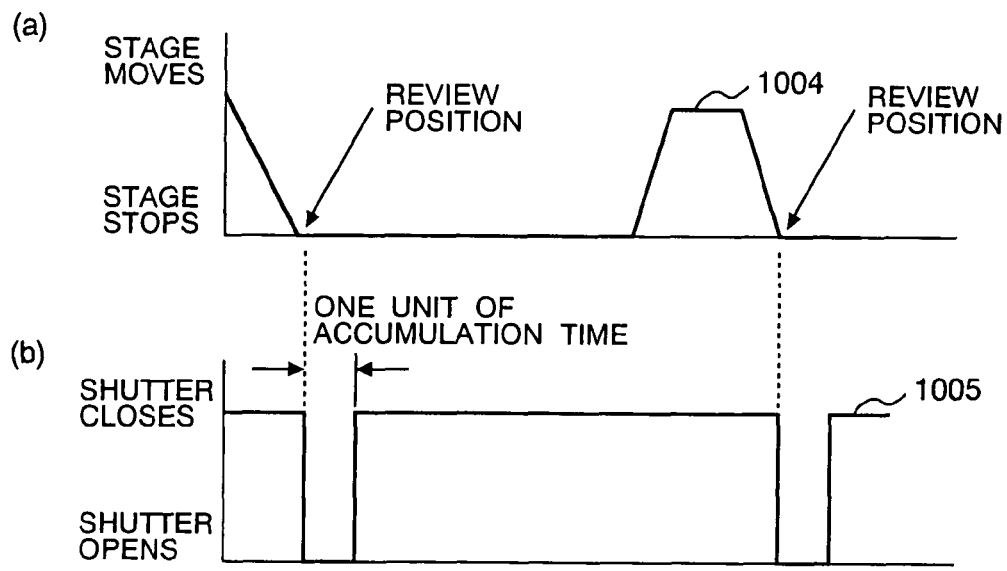
FIG. 31 is diagrams illustrating moves of a stage, and opening and closing of a shutter, at the time of inspection (review) according to the present invention.

In addition, other than at the time of inspection, there is also a possibility that the sample will be damaged. This is, for example, at the time of review with the object of checking the arrangement and shape of a pattern to set inspection conditions, or with the object of checking the result of the inspection. At the time of inspection, the quantity of light incident on the sample 1 causes little damage because of high-speed scan operation. However, at the time of review using a detector 28 and the like, the sample 1 is kept at a standstill to obtain an image. Accordingly, a period of time during which the sample 1 is irradiated with illumination light becomes longer. For this reason, in the review recipe setting screen 3300b constituting the recipe setting unit shown in FIG. 34, it is desirable to control the shutter 4 according to an instruction from the CPU 212 so that the shutter 4 is opened, only for a period of time T during which a review image is captured, at a review position where a check is made as to the arrangement, and a shape, of a pattern, and the result of the inspection, which are set for the CPU 212. More specifically, FIG. 31 illustrates an embodiment showing the relationship between the irradiation of illumination light and the review at the time of the review in which the above-mentioned information is checked.

FIG. 31(a) is a chart illustrating move timing of the stage 2; and FIG. 31(b) is a chart illustrating a drive pattern of the shutter 4. For example, in FIG. 31(a), the stage 2 moves to a review position, and then the stage 2 moves again at timing 1004. On the assumption that a position at which the stage 2 stops is a review position, the shutter drive circuit 5 is operated so as to open and close the shutter 4 at timing 1005 shown in FIG. 31(b). That is, when closing the shutter 4, it is not necessary to intercept the light completely, but it is needed only to remarkably reduce the quantity of irradiated light. If for example a CCD camera is used as the detector 28, this one unit of accumulation time T is treated as open time. By irradiating the sample 1 with light only at a required review position, it is possible to limit the quantity of light to be incident on the sample 1. As a matter of course, this quantity of light does not cause the damage to the sample 1.

Additionally, for the purpose of checking whether or not the inspection result after the inspection, which is set as a review recipe, is correct, a review may be made in the main-body control circuit 50 using for example the detector 28. In such a case, it is conceivable that the result changes a focus position (for example, a Z stage 2' is moved) before making the review. In this case, checking the same position many times causes the sample 1 to be continuously irradiated with light, which leads to the damage to the sample 1.

Figure 32:
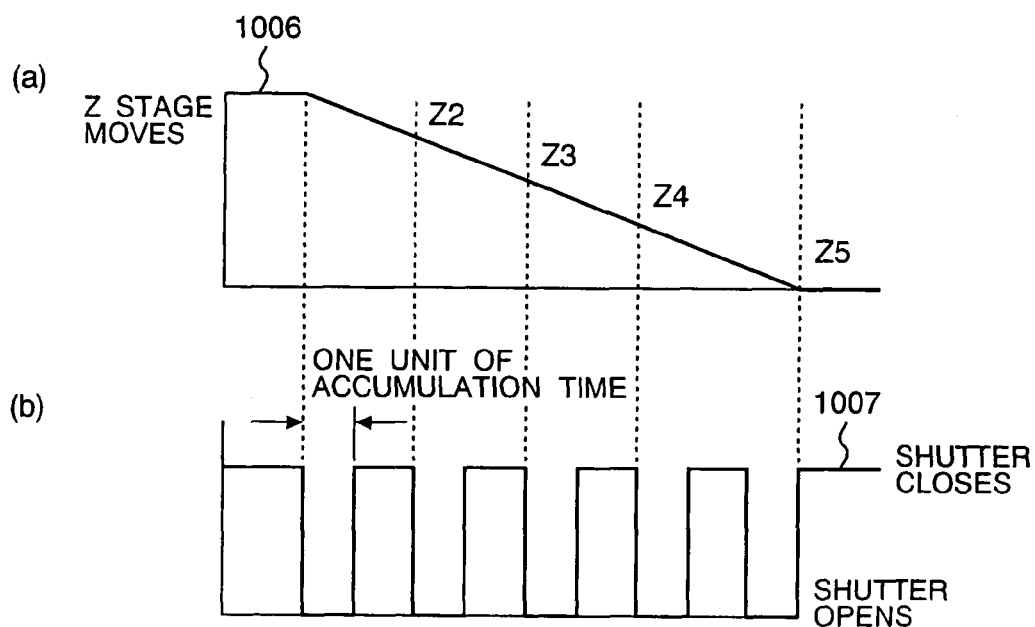
FIG. 32 is diagrams illustrating moves of a stage, and opening and closing of a shutter, when moving a Z stage to make a review according to the present invention.

FIG. 32 illustrates an embodiment showing the relationship between the irradiation of illumination light and the review when the focus position changes. FIG. 32(a) is a chart illustrating move timing of the Z stage 2'; and FIG. 32(b) is a chart illustrating a drive pattern of the shutter 4. For example, in FIG. 32(a), the Z stage 2' moves to a review position, and then continuously moves at timing 1006. At timing 1007 shown in FIG. 32(b), the shutter drive circuit 5 is operated so as to open and close the shutter 4. That is, when closing the shutter 4, it is not necessary to intercept the light completely, but it is needed only to remarkably reduce the quantity of irradiated light. At this time, consecutively storing in a memory 220 images reviewed by the detector 28 allows the main-body control circuit 50 to review a change of the sample 1 when moving a focus. If a review is required again at this position, which is set as a review recipe, the review becomes possible at the position where the focus has changed, without irradiating the sample 1 with light again. This can avoid the damage to the sample 1.

Figure 33:
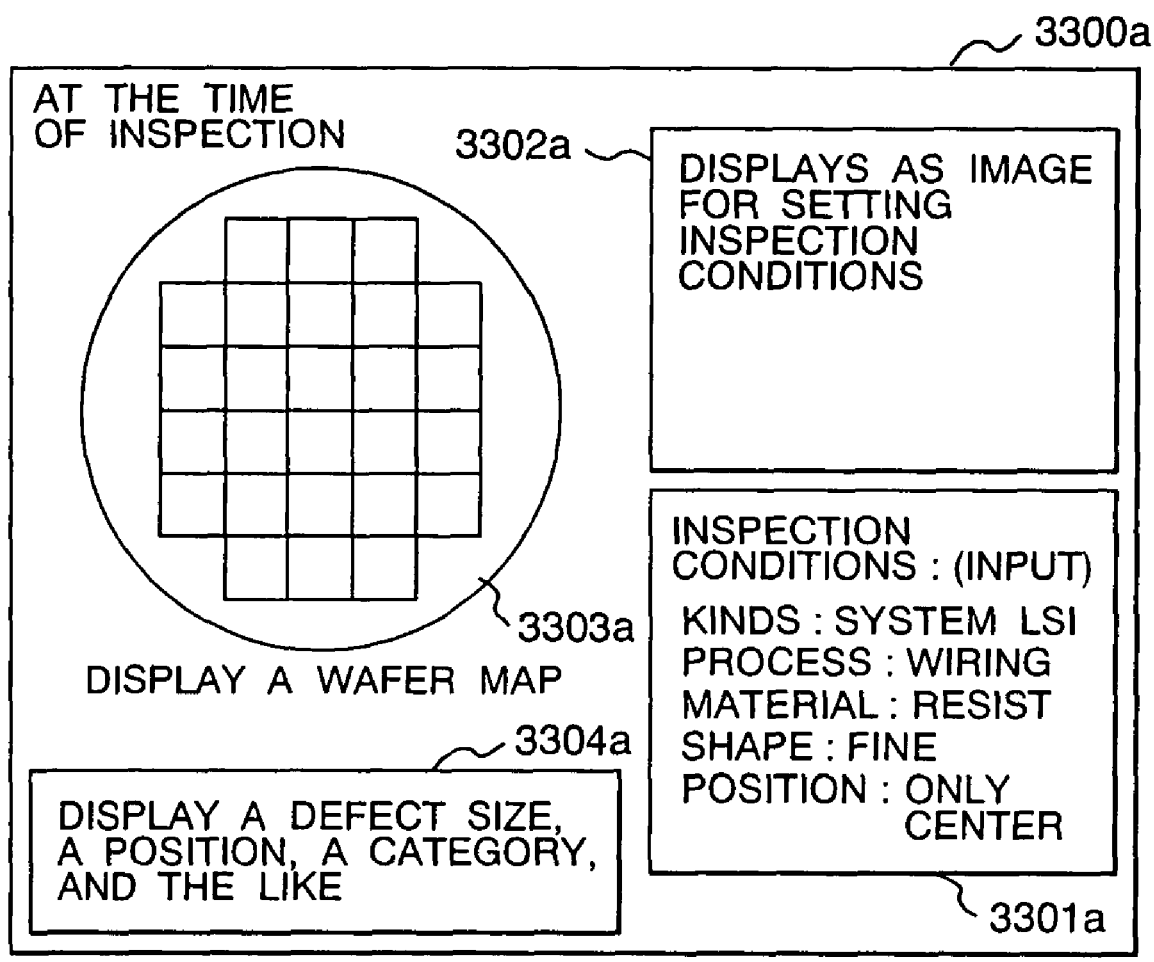
FIG. 33 is a diagram illustrating an inspection recipe setting screen for setting an inspection recipe according to the present invention.
Figure 34:
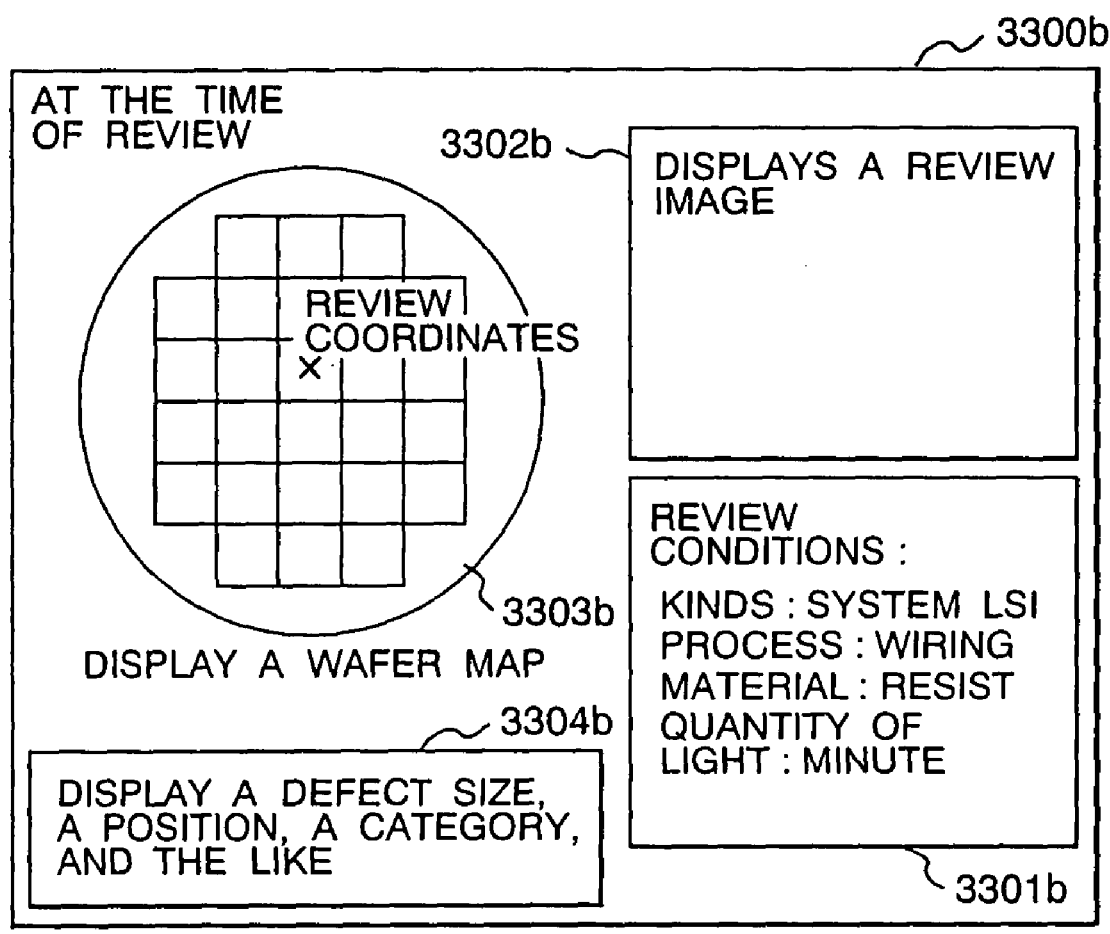
FIG. 34 is a diagram illustrating a review recipe setting screen for setting a review recipe according to the present invention.

In addition, depending on a kind of the sample 1, there exists a material for which the damage need not be taken into consideration. For example, the material is $SiN_4$. When inspecting and reviewing such a material, the above-mentioned control may become unnecessary in some cases. In order to allow the CPU 212 of the main-body control circuit 50 to set irradiation conditions according to such a material, a state of the sample (including a surface state, the quality of material, film thickness, a damage condition, a kind of chip, a state of chip array, and a process) is set beforehand in for example a recipe in which inspection conditions are set, as shown in FIGS. 33 and 34, by use of design data and the like stored in the storing unit 208. As a result, it is possible to determine the inspection conditions including the irradiation conditions.

In other words, by entering and inputting the state of the sample on a recipe setting screen 1008 shown in FIGS. 33 and 34, which is displayed in the display unit 209, it is possible to set the inspection conditions for the CPU 121, and also to store the inspection conditions in the storing unit 208. FIG. 33 is a diagram illustrating an inspection recipe setting screen used for inspection, which is displayed in the display unit 209 and is used to input and set an inspection recipe for the CPU 121. FIG. 34 is a diagram illustrating a review recipe setting screen used for review, which is displayed in the display unit 209 and is used to input and set a review recipe for the CPU 121.

The CPU 121 displays an image for setting inspection conditions 3302a on the inspection recipe setting screen 3300a shown in FIG. 33, which is the recipe setting unit. Using the inspection recipe setting screen 3300a, inspection conditions 3301a are inputted and set. The inspection conditions 3301a includes a kind of a sample, a process of the sample, a material of a surface of the sample, a shape of a pattern to be inspected, and a place of inspection. After that, on the basis of the design data by kind of sample, which has been inputted and stored in the storing unit 208, the CPU 121 creates chip array data of the sample in accordance with a kind of the set sample and the like. Then it displays the chip array data as a wafer map 3303a, and also displays information 3304a including a defect size, a position, and a category, which are the result of the inspection.

Moreover, the CPU 121 displays a review image 3302b, which is specified by review coordinates, on the review recipe setting screen 3300b shown in FIG. 34 as the recipe setting unit. Using the review recipe setting screen 3300b, review conditions 3301b are inputted and set. The review conditions 3301b includes a kind of a sample, a process of the sample, a material of a surface of the sample, and the quantity of light. After that, on the basis of the design data by kind of sample, which has been inputted and stored in the storing unit 208, the CPU 121 creates chip array data of the sample in accordance with to a kind of the set sample and the like. Then it displays the chip array data as a wafer map 3303b, and also displays information 3304b including a defect size, a position, and a category, which are the result of the review.

Thus, at the time of both inspection and review, on the basis of recipe conditions (inspection conditions and review conditions) that have been set by the recipe setting unit, the CPU 121 determines illumination conditions (in particular, the quantity of light) for a move of the stage 2 so that the illumination optical system and the sample 1 suffer no damage, and thereby the CPU 121 controls the shutter 4 or the ND filter 11 so as to meet the illumination conditions.

Figure 35:
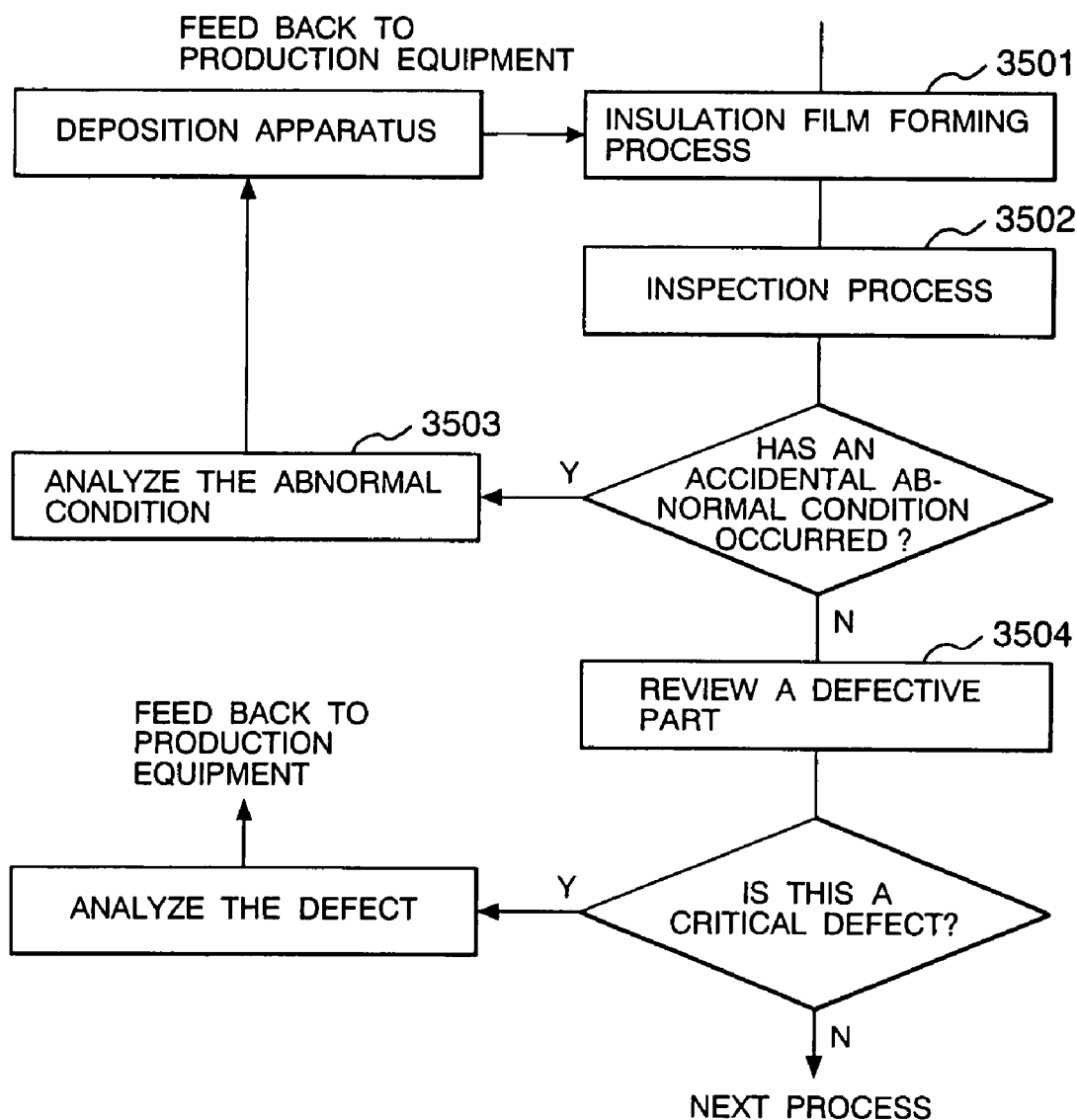
FIG. 35 is a flowchart illustrating effects produced in the manufacturing process according to the present invention.

What will be described next with reference to FIG. 35 is an effective method for utilizing the above-mentioned inspected-pattern defect inspecting apparatus in a semiconductor forming process. A semiconductor such as LSI is formed through various processes. More specifically, a device is formed by laminating the patterns that are transferred in respective processes. Even one defect such as a broken wire or short circuit in one of the processes will cause the subsequent processes to result in failure. For this reason, in an inspection process 3502, a defect on insulation film formed in, for example, an insulation film forming process 3501 is inspected using the inspected-pattern defect inspecting apparatus according to the present invention to check whether or not an accidental abnormal condition has occurred. Then, analyzing the abnormal condition in a process 3503 enables feedback to, for example, an apparatus by which insulation film is deposited, and a CMP (Chemical Mechanical Polishing) apparatus for machining a surface so that it becomes flat. Moreover, a detected defective part is reviewed (in a process 3504). If the defective part does not contain a critical defect, the next process is performed just as it is to reduce a percent defective. If a critical defect is found, the defect is analyzed by use of a review tool (a review machine) or the like. If it is judged to be failure, the failure is quickly fed back to production equipment, which prevents a large number of failures from occurring.

As described above, by use of ultraviolet light with a wavelength such as 266 nm, 248 nm, or 192 nm, it is possible to achieve defect inspection of a device having a rule of about 70 nm. In addition, by irradiating a sample with required minimum light, it becomes possible to apply it to inspection of a material that generates a concern about the damage to the sample in resist, Cu Damascene, or the like, as an object to be inspected. Moreover, even if there is no pattern as an object to be inspected, a speckle does not occur. Therefore, even if a comparison is made between a reference image and a detected image, a false report is not generated, making it possible to perform inspection.

Incidentally, ultraviolet light with a wavelength of about 365 nm or less, which is used as illumination light, has high optical energy. Accordingly, when an optical element is irradiated with this ultraviolet light, a pollutant including organic matter is resolved or reacted by the energy of ultraviolet light, and then adheres to a surface. Also for the purpose of coping with this problem, irradiating the optical system with required minimum light can also avoid the damage to the optical system. Moreover, providing a means for compulsorily exhausting air from a surface of an optical component using an unillustrated method, or a means for compulsorily spraying air, makes it possible to prevent the optical component from degrading.

Additionally, although the bright field optical system has been described in the embodiment, similar effects can also be obtained even if a confocal microscope is configured as the detection optical system.

According to the embodiments of the present invention as described above, both inspection and review that are set using the recipe setting unit including the recipe setting screen 3300. At this time, it is possible to irradiate a sample with ultraviolet light having a wavelength of about 365 nm or less with its energy being reduced to a minimum level. Accordingly, the inspection becomes possible without causing a pattern to shrink or expand relative to the resist used for a shorter wavelength.

In addition, according to the embodiments of the present invention, even in the case of a chip in which a memory part having a narrow line width, a rough wiring part, and the like, are mixed, such as a system LSI that is set by the recipe setting unit including the recipe setting screen 3300, illuminating such a chip with ultraviolet light having a wavelength of 365 nm or less does not cause heat to accumulate in part of the chip, and consequently the peeling of a pattern called stress migration does not occur due to the bimetal effect. Moreover, since not only the peeling of soft film with low mechanical strength like a material with low conductivity (low-k), but also diffusion by heat, chemical change by ultraviolet light of impurities, and the like, produce no effects, a bad influence is not exerted on the device. Further, it is also possible to reduce the influence on a limit of the heat capacity that is acceptable for a device, which is called thermal budget. Therefore, by use of a laser light source which is illumination with a shorter wavelength that is indispensable for increasing the resolution, and which is advantageous for its practical use, it is possible to obtain with higher sensitivity and at higher speed an image having the quality that is the same as or higher than that of a usual electric discharge tube illumination. Consequently, a minute defect can be detected with high sensitivity.

According to the present invention, the effect produced is that it is possible to detect with high resolution a minute circuit pattern, which seldom causes the damage to a sample and an optical system, and thereby a defect can be detected.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description and all changes which come within the meaning and range of equivalency of the claims are therefore intended to be embraced therein.

The invention claimed is:

1. A pattern defect inspection apparatus comprising:
a recipe setting unit for setting an inspection recipe and/or a review recipe;
an illumination optical system including:
  a laser light source for emitting a laser toward a sample according to the inspection recipe set by the recipe setting unit, and
  a shutter for selectively restricting passage of the laser emitted from the laser light source; and
a detection optical system for imaging a reflected light image with light reflected from the sample to detect an image signal,
wherein the shutter opens during image capture at the time of inspecting and at a period time during image capture at the time of reviewing, and
wherein the detection optical system includes a backside illumination type image sensor which detects the image signal by receiving the reflected light from a front side of the sample at a backside of the image sensor while the shutter is opening.

2. A pattern defect inspection apparatus according to claim 1, wherein the backside illumination type image sensor is a time delay integration image sensor.

3. A pattern defect inspection apparatus according to claim 1, wherein the backside illumination type image sensor has an antiblooming characteristic.

* * * * *